US012775891B2

(12) United States Patent
Chang et al.

(10) Patent No.: US 12,775,891 B2
(45) Date of Patent: Oct. 27, 2026

(54) SYSTEM AND METHOD FOR CALCULATING TRANSPORT ROUTES

(71) Applicants: Board of Regents, The University of Texas System, Austin, TX (US); The University of North Carolina at Chapel Hill, Chapel Hill, NC (US)

(72) Inventors: Joshua Chang, Pflugerville, TX (US); David Paydarfar, Austin, TX (US); Daniel Paydarfar, Austin, TX (US); Peter Mucha, Chapel Hill, NC (US)

(73) Assignees: Board of Regents, The University of Texas System, Austin, TX (US); The University of North Carolina at Chapel Hill, Chapel Hill, NC (US)

( * ) Notice: Subject to any disclaimer, the term of this patent is extended or adjusted under 35 U.S.C. 154(b) by 315 days.

(21) Appl. No.: 18/558,090

(22) PCT Filed: Apr. 29, 2022

(86) PCT No.: PCT/US2022/027010
§ 371 (c)(1),
(2) Date: Oct. 30, 2023

(87) PCT Pub. No.: WO2022/232561
PCT Pub. Date: Nov. 3, 2022

(65) Prior Publication Data

US 2024/0202613 A1 Jun. 20, 2024

Related U.S. Application Data

(60) Provisional application No. 63/182,140, filed on Apr. 30, 2021.

(51) Int. Cl.
*G06Q 10/047* (2023.01)
*G16H 50/50* (2018.01)

(52) U.S. Cl.
CPC .......... *G06Q 10/047* (2013.01); *G16H 50/50* (2018.01)

(58) Field of Classification Search
CPC ........ G16H 50/50; G16H 20/40; G16H 40/20; G06Q 50/40
See application file for complete search history.

(56) References Cited

U.S. PATENT DOCUMENTS 8,036,822 B2 * 10/2011 Ho .................... G01C 21/3407
340/995.13
8,332,247 B1 12/2012 Bailey
(Continued)

OTHER PUBLICATIONS

Froehler, M. T., Saver, J. L., Zaidat, O. O., Jahan, R., Aziz-Sultan, M. A., Klucznik, R. P., . . . & Mueller-Kronast, N. H. (2017). Interhospital transfer before thrombectomy is associated with delayed treatment . . . Circulation, 136(24), 2311-2321. (Year: 2017).*
(Continued)

*Primary Examiner* — Hitesh Patel
*Assistant Examiner* — Tabitha Kress
(74) *Attorney, Agent, or Firm* — Riverside Law LLP

(57) ABSTRACT

A method of calculating a set of desired transport routes for a stroke patient comprises selecting a set of destination points, comprising a first stroke center and a second stroke center, generating a set of infarct core growth models for stroke patients along at least a first path from a starting point to the first stroke center followed by an optional trip to the second stroke center, and a second path from the starting point to the second stroke center, varying a set of parameters of the stroke patients, calculating a model of patient outcomes from each origin point, and designating whether the first path or the second path is preferable based on the probabilistic model. A system for displaying a desired transport route for a stroke patient and a method of calculating a
(Continued)

preferred location for a mobile treatment unit in a geographic region are also described.

31 Claims, 17 Drawing Sheets

(56) References Cited

U.S. PATENT DOCUMENTS

| | | | | |
|---|---|---|---|---|
| 10,692,591 | B2 * | 6/2020 | Huang | G16H 10/60 |
| 10,916,346 | B2 | 2/2021 | Menon | |
| 2019/0304606 | A1 * | 10/2019 | Menon | A61B 5/0042 |
| 2020/0160121 | A1 * | 5/2020 | Parasrampuria | G06N 5/022 |
| 2020/0206517 | A1 | 7/2020 | Martin | |

OTHER PUBLICATIONS

Grekousis, G., & Photis, Y. N. (2014). Analyzing high-risk emergency areas with GIS and neural networks: The case of Athens, Greece. The Professional Geographer, 66(1), 124-137. (Year: 2014).*

Klepaczko, A., Szczypiński, P., Deistung, A., Reichenbach, J. R., & Materka, A. (2016). Simulation of MR angiography imaging for validation of cerebral arteries segmentation algorithms. Computer methods and programs in biomedicine, 137, 293-309. (Year: 2016).*

Rajagopalan, H. K., Saydam, C., & Xiao, J. (2008). A multiperiod set covering location model for dynamic redeployment of ambulances. Computers & Operations Research, 35(3), 814-826. (Year: 2008).*

Hosseini, M., Berlin, R. B., & Sha, L. (Aug. 2017). Physiology-aware rural ambulance routing. In 2017 IEEE International Conference on Healthcare Informatics (ICHI) (pp. 332-337). IEEE. (Year: 2017).*

González, R. G., Silva, G. S., He, J., Sadaghiani, S., Wu, O., & Singhal, A. B. (2020). Identifying Severe Stroke Patients Likely to Benefit From Thrombectomy Despite Delays of up to a Day. Scientific reports, 10(1), 4008. (Year: 2020).*

Abilleira S, Ribera A, Cardona P, Rubiera M, López-Cancio E, Amaro S, Rodríguez-Campello A, Camps-Renom P, Cánovas D, Angels de Miquel M, et al. Outcomes After Direct Thrombectomy or Combined Intravenous and Endovascular Treatment Are Not Different. Stroke. 2017;48(2):375-378. doi:10.1161/STROKEAHA.116.015857.

Anderson CS, Huang Y, Arima H, Heeley E, Skulina C, Parsons MW, Peng B, Li Q, Su S, Tao QL, et al.; Interact Investigators. Effects of early intensive blood pressure-lowering treatment on the growth of hematoma and perihematomal edema in acute intracerebral hemorrhage: Intensive Blood Pressure Reduction in Acute Cerebral Haemorrhage Trial (Interact). Stroke. 2010;41(2):307-312. doi:10.1161/STROKEAHA.109.561795.

Bandera E, Botteri M, Minelli C, Sutton A, Abrams K, Latronico N. Cerebral Blood Flow Threshold of Ischemic Penumbra and Infarct Core in Acute Ischemic Stroke. Stroke. 2006;37(5):1334-1339. doi:10.1161/01.STR.0000217418.29609.22.

Banks JL, Marotta CA. Outcomes Validity and Reliability of the Modified Rankin Scale: Implications for Stroke Clinical Trials. Stroke. 2007;38(3):1091-1096. doi:10.1161/01.STR.0000258355.23810.c6.

Christoforidis GA, Vakil P, Ansari SA, Dehkordi FH, Carroll TJ. Impact of Pial Collaterals on Infarct Growth Rate in Experimental Acute Ischemic Stroke. Am J Neuroradiol. 2017;38(2):270. doi:10.3174/ajnr.A5003.

Dozois A, Hampton L, Kingston CW, Lambert G, Porcelli TJ, Sorenson D, Templin M, VonCannon S, Asimos AW. Plumber Study (Prevalence of Large Vessel Occlusion Strokes in Mecklenburg County Emergency Response). Stroke. 2017;48(12):3397-3399. doi:10.1161/STROKEAHA.117.018925.

Ernst M, Boers AM, Aigner A, Berkhemer O, Yoo AJ, Roos YB, Dippel DW, van der Lugt A, van Oostenbrugge R, van Zwam WH, et al. Association of Computed Tomography Ischemic Lesion Location With Functional Outcome in Acute Large Vessel Occlusion Ischemic Stroke. Stroke. 2017;48(9):2426-2433. doi:10.1161/STROKEAHA.117.017513.

Fischer U, Kaesmacher J, Pereira VM, Chapot R, Siddiqui AH, Froehler MT, Cognard C, Furlan AJ, Saver JL, Gralla J. Direct Mechanical Thrombectomy Versus Combined Intravenous and Mechanical Thrombectomy in Large-Artery Anterior Circulation Stroke: A Topical Review. Stroke. 2017;48(10):2912-2918. doi:10.1161/STROKEAHA.117.017208.

Fonarow GC, Zhao X, Smith EE, Saver JL, Reeves MJ, Bhatt DL, Xian Y, Hernandez AF, Peterson ED, Scwhamm LH. Door-to-Needle Times for Tissue Plasminogen Activator Administration and Clinical Outcomes in Acute Ischemic Stroke Before and After a Quality Improvement Initiative. JAMA. 2014;311(16):1632-1640. doi:10.1001/jama.2014.3203.

Gomez CR. Time Is Brain: The Stroke Theory of Relativity. J Stroke Cerebrovasc Dis off J Natl Stroke Assoc. 2018;27(8):2214-2227. doi:10.1016/j.jstrokecerebrovasdis.2018.04.001.

Goyal M, Demchuk AM, Menon BK, Eesa M, Rempel JL, Thornton J, Roy D, Jovin TG, Willinsky RA, Sapkota BL, et al. Randomized Assessment of Rapid Endovascular Treatment of Ischemic Stroke. N Engl J Med. 2015;372(11):1019-1030. doi:10.1056/NEJMoa1414905.

Goyal M, Menon B, van Zwam WH, Dippel DW, Mitchell P, Demchuk A, Dávalos A, Majoie C, van der Lugt A, de Miquel MA, et al. Endovascular thrombectomy after large-vessel ischaemic stroke: a meta-analysis of individual patient data from five randomised trials. Lancet Lond Engl. 2016;387(10029):1723-1731. doi:10.1016/S0140-6736(16)00163-X.

Gratz PP, Schroth G, Gralla J, Mattle HP, Fischer U, Jung S, Mordasini P, Hsieh K, Verma RK, Weisstanner C, El-Koussy M. Whole-Brain Susceptibility-Weighted Thrombus Imaging in Stroke: Fragmented Thrombi Predict Worse Outcome. AJNR Am J Neuroradiol. 2015;36(7):1277-1282. doi:10.3174/ajnr.A4275.

Hemphill JC 3rd, Greenberg SM, Anderson CS, Becker K, Bendok BR, Cushman M, Fung GL, Goldstein JN, Macdonald RL, Mitchell PH, Scott PA, Selim MH, Woo D; on behalf of the American Heart Association Stroke Council, Council on Cardiovascular and Stroke Nursing, and Council on Clinical Cardiology. Guidelines for the management of spontaneous intracerebral hemorrhage: a guideline for healthcare professionals from the American Heart Association/American Stroke Association. Stroke. 2015;46:2032-2060.

Higashida R, Alberts MJ, Alexander DN, Crocco TJ, Demaerschalk BM, Derdeyn CP, Goldstein LB, Jauch EC, Mayer SA, Meltzer NM, et al. Interactions Within Stroke Systems of Care. Stroke. 2013;44(10):2961-2984. doi:10.1161/STR.0b013e3182a6d2b2.

Holodinsky JK, Williamson TS, Demchuk AM, Zhao H, Zhu L, Francis MJ, Goyal M, Hill MD, Kamal N. Modeling Stroke Patient Transport for All Patients With Suspected Large-Vessel Occlusion. JAMA Neurol. 2018;75(12):1477-1486. doi:10.1001/jamaneurol.2018.2424.

Holodinsky JK, Williamson TS, Kamal N, Mayank D, Hill MD, Goyal M. Drip and Ship Versus Direct to Comprehensive Stroke Center. Stroke. 2017;48(1):233-238. doi:10.1161/STROKEAHA.116.014306.

International Search Report and Written Opinion issued in App. No. PCT/US22/27010, mailing date Dec. 5, 2022, 12 pages.

Jahan R, Saver JL, Schwamm LH, Fonarow GC, Lian L, Matsouaka RA, Xian Y, Holms DN, Peterson ED, Yavagal D, et al. Association Between Time to Treatment With Endovascular Reperfusion Therapy and Outcomes in Patients With Acute Ischemic Stroke Treated in Clinical Practice. JAMA. 2019;322(3):252-263. doi:10.1001/jama.2019.8286.

Malhotra K, Gornbein J, Saver JL. Ischemic Strokes Due to Large-Vessel Occlusions Contribute Disproportionately to Stroke-Related Dependence and Death: A Review. Front Neurol. 2017;8:651. doi:10.3389/fneur.2017.00651.

Marc Ribo. European Stroke Organisation-World Stroke Organisation (ESO-WSO) Conference 2020: Presented Nov. 7, 2020. First Press Release. https://eso-wso-conference.org/media-portal/, 5 pages.

Markus R, Reutens DC, Kazui S, Read S, Wright P, Chambers BR, Sachinidis JI, Tochon-Danguy HJ, Donnan GA. Topography and Temporal Evolution of Hypoxic Viable Tissue Identified by 18F-

(56) References Cited

OTHER PUBLICATIONS

Fluoromisonidazole Positron Emission Tomography in Humans After Ischemic Stroke. Stroke. 2003;34(11):2646-2652. doi:10.1161/01.STR.0000094422.74023.FF.
Mayer SA, Brun NC, Begtrup K, Broderick J, Davis S, Diringer MN, Skolnick BE, Thorsten S; Fast Trial Investigators. Efficacy and safety of recombinant activated factor VII for acute intracerebral hemorrhage. N Engl J Med. 2008;358(20):2127-2137. doi:10.1056/NEJMoa0707534.
Mendelow AD, Gregson BA, Rowan EN, Murray GD, Gholkar A, Mitchell PM; Stich II Investigators. Early surgery versus initial conservative treatment in patients with Spontaneous Supratentorial Lobar Intracerebral Haematomas (Stich II): a randomised trial. Lancet. 2013;382(9890):397-408. doi10.1016/S0140-6736(13)60986-1.
Menon BK, Al-Ajlan FS, Najm M, Puig J, Castellanos M, Dowlatshahi D, Calleja A, Sohn S, Ahn SH, Poppe A, et al. Association of Clinical, Imaging, and Thrombus Characteristics With Recanalization of Visible Intracranial Occlusion in Patients With Acute Ischemic Stroke. JAMA. 2018;320(10):1017-1026. doi:10.1001/jama.2018.12498.
Menon BK, Sajobi TT, Zhang Y, Rempel JL, Shuaib A, Thornton J, Williams D, Roy D, Poppe AY, Jovin TG, et al. Analysis of Workflow and Time to Treatment on Thrombectomy Outcome in the Endovascular Treatment for Small Core and Proximal Occlusion Ischemic Stroke (Escape) Randomized, Controlled Trial. Circulation. 2016;133(23):2279-2286. doi:10.1161/CIRCULATIONAHA.115.019983.
Milne MS, Holodinsky JK, Hill MD, Nygren A, Qui C, Goyal M, Kamal N. Drip 'n Ship Versus Mothership for Endovascular Treatment. Stroke. 2017;48(3):791-794. doi:10.1161/STROKEAHA.116.015321.
Muchada M, Rodriguez-Luna D, Pagola J, Flores A, Sanjuan E, Meler P, Boned S, Alvarez-Sabin J, Ribo M, Molina CA, Rubiera M. Impact of Time to Treatment on Tissue-Type Plasminogen Activator-Induced Recanalization in Acute Ischemic Stroke. Stroke. 2014;45(9):2734-2738. doi:10.1161/STROKEAHA.114.006222.
Powers WJ, Rabinstein AA, Ackerson T, Adeoye MO, Bambakidis NC, Becker K, Biller J, Brown M, Demaerschalk BM, Hoh B, et al. Guidelines for the Early Management of Patients With Acute Ischemic Stroke: 2019 Update to the 2018 Guidelines for the Early Management of Acute Ischemic Stroke: A Guideline for Healthcare Professionals From the American Heart Association/American Stroke Association. Stroke. 2019;50(12):e344-e418. doi:10.1161/STR.0000000000000211.
Prabhakaran S, Ruff I, Bernstein RA. Acute stroke intervention: a systematic review. JAMA. 2015;313(14):1451-1462. doi:10.1001/jama.2015.3058.
Rivers CS, Wardlaw JM, Armitage PA, Bastin ME, Carpenter TK, Cvoro V, Hand PJ, Dennnis MS. Do Acute Diffusion- and Perfusion-Weighted MRI Lesions Identify Final Infarct Volume in Ischemic Stroke? Stroke. 2006;37(1):98-104. doi:10.1161/01.STR.0000195197.66606.bb.
Saver JL, Goyal M, van der Lugt A, Menon BK, Majoie CB, Dippel DW, Campbell BC, Nogueira RG, Demchuk AM, Tomasello A, et al. Time to Treatment With Endovascular Thrombectomy and Outcomes From Ischemic Stroke: A Meta-analysis. JAMA. 2016;316(12):1279-1289. doi:10.1001/jama.2016.13647.
Saver JL. Time is brain—quantified. Stroke. 2006;37(1):263-266. doi:10.1161/01.STR.0000196957.55928.ab.
Seners P, Turc G, Naggara O, Henon H, Piotin M, Arquizan C, Cho TH, Narata AP, Lapergue B, Richard S, et al. Post-Thrombolysis Recanalization in Stroke Referrals for Thrombectomy. Stroke. 2018;49(12):2975-2982. doi:10.1161/STROKEAHA.118.022335.
Southerland AM, Johnston KC, Molina CA, Selim MH, Kamal N, Goyal M. Suspected Large Vessel Occlusion. Stroke. 2016;47(7):1965-1967. doi:10.1161/STROKEAHA.115.011149.
Steiner T, Poli S, Griebe M, Hüsing J, Hajda J, Freiberger A, Bendszus M, Bösel J, Christensen H, Dohmen C, et al. Fresh frozen plasma versus prothrombin complex concentrate in patients with intracranial haemorrhage related to vitamin K antagonists (Inch): a randomised trial. Lancet Neurol. 2016;15(6):566-573. doi:10.1016/S1474-4422(16)00110-1.
Suzuki K, Matsumaru Y, Takeuchi M, Morimoto M, Kanazawa R, Takayama Y, Kamiya Y, Shigeta K, Okubo S, Hayakawa M, et al. Effect of Mechanical Thrombectomy Without vs With Intravenous Thrombolysis on Functional Outcome Among Patients With Acute Ischemic Stroke: The Skip Randomized Clinical Trial. JAMA. 2021;325(3):244-253. doi:10.1001/jama.2020.23522.
Texas Health and Human Services. Requirements for Stroke Facility Designation. Texas: Texas Department of State Health Services; 2008, 8 pages.
United States Census Bureau. Tiger/Line Shapefiles with Selected Demographic and Economic Data. Last revised Dec. 2019. Retrieved from: https://www.census.gov/geographies/mapping-files/2010/geo/tiger-data. 4 pages.
Venema E, Lingsma HF, Chalos V, Mulder MJ, Lahr MM, van der Lugt A, van Es AC, Steyerberg EW, Hunink MM, Dippel DW, et al. Personalized Prehospital Triage in Acute Ischemic Stroke. Stroke. 2019;50(2):313-320. doi:10.1161/STROKEAHA.118.022562.
Vogt G, Laage R, Shuaib A, Schneider A. Initial lesion volume is an independent predictor of clinical stroke outcome at day 90: an analysis of the Virtual International Stroke Trials Archive (VISTA) database. Stroke. 2012;43(5):1266-1272. doi:10.1161/STROKEAHA.111.646570.
Wang X, Arima H, Heeley E, Delcourt C, Huang Y, Wang J, Stapf C, Robinson T, Woodward M, Chalmers J, Anderson CS; Interact2 Investigators. Magnitude of blood pressure reduction and clinical outcomes in acute intracerebral hemorrhage: intensive blood pressure reduction in acute cerebral hemorrhage trial study. Hypertension. 2015;65(5):1026-1032. doi:10.1161/HYPERTENSIONAHA.114.05044.
Xu Y, Parikh NS, Jiao B, Willey JZ, Boehme AK, Elkind MS. Decision Analysis Model for Prehospital Triage of Patients With Acute Stroke. Stroke. 2019;50(4):970-977. doi:10.1161/STROKEAHA.118.023272.
Zanette EM, Roberti C, Mancini G, Pozzilli C, Bragoni M, Toni D. Spontaneous Middle Cerebral Artery Reperfusion in Ischemic Stroke. Stroke. 1995;26(3):430-433. doi:10.1161/01.STR.26.3.430.
Zhao H, Coote S, Pesavento L, Churilov L, Dewey HM, Davis SM, Campbell BCV. Large Vessel Occlusion Scales Increase Delivery to Endovascular Centers Without Excessive Harm From Misclassifications. Stroke. 2017;48(3):568-573. doi:10.1161/STROKEAHA.116.016056.

* cited by examiner

SYSTEM AND METHOD FOR CALCULATING TRANSPORT ROUTES

CROSS-REFERENCE TO RELATED APPLICATIONS

This application is a 35 U.S.C. § 371 national phase application claiming priority to International Application No. PCT/2022/027010, filed Apr. 29, 2022, which claims priority to U.S. Provisional Patent Application No. 63/182,140 filed Apr. 30, 2021, both of which are incorporated herein by reference in their entirety.

BACKGROUND OF THE INVENTION

Rapid neuronal loss from acute ischemic stroke occurs as the infarct core grows within its ischemic penumbra. The duration of ischemic stroke evolution is highly variable, ranging between 6 to 18 hours for large vessel occlusions, and the degree of collateral blood flow is a major determinant of the rate at which an infarct core achieves full ischemic volume. Large vessel occlusions (LVO) are the most severe stroke-type, with an incidence rate of 25% of ischemic stroke cases. Endovascular thrombectomy (EVT) is the primary treatment method for LVOs and can be administered at a comprehensive stroke center (CSC). Non-LVOs, comprising of lacunar strokes related to small vessel disease as well as small emboli, comprise 75% of ischemic stroke cases, and thrombolysis with intravenous tissue plasminogen activator (tPA) is the standard treatment for qualifying patients who present symptoms up to 4.5 hours prior at either a primary stroke center (PSC) or a CSC. Stroke outcomes are time-dependent, so it is pertinent for a suspected stroke patient to receive suitable treatment quickly.

If a CSC is the closest stroke center to the patient pickup location in terms of transport time, then the patient is taken directly there, as the best treatment options for any stroke type are available. When a PSC is closer to the patient pickup location than a CSC, emergency medical services (EMS) must decide between two strategies of emergency stroke transport. The first, referred to herein as Drip and Ship (DNS), takes the patient directly to the closer PSC where they are able to receive cerebrovascular imaging and tPA, then proceeds to the CSC if an LVO is identified. The second strategy, referred to herein as Mothership (MS) bypasses the closer PSC for a more distant but EVT-capable CSC. While there are cases in which the optimal emergency transport strategy is clear (e.g. a patient with unequivocal signs and symptoms of a non-LVO), EMS is often unable to ascertain a patient's stroke type with certainty given current field-testing capabilities. For these patients, the optimal transport strategy is ambiguous.

Thus, there is a need in the art for a system and method for quickly and accurately determining the most effective transport strategy for a stroke patient. The disclosed novel framework satisfies this need.

SUMMARY OF THE INVENTION

In one aspect, a method of calculating a set of desired transport routes for a stroke patient comprises selecting a set of destination points, the set of destination points comprising at least a first stroke center and a second stroke center, from a patient starting point, generating a set of simulated infarct core growth models for simulated stroke patients along at least a first path from the patient starting point to the first stroke center followed by an optional trip to the second stroke center, and a second path from the starting point directly to the second stroke center, varying a set of parameters of the simulated stroke patients across the set of simulated infarct core growth models, calculating a probabilistic model of patient outcomes from the set of simulated infarct core growth models from the starting point, and designating whether the first path or the second path is preferable based on the probabilistic model.

In one embodiment, the method further comprises selecting a set of origin points, from each origin point of the set of origin points, generating a set of simulated infarct core growth models for simulated stroke patients along at least the first path and the second path, calculating the probabilistic model of patient outcomes from the set of simulated infarct core growth models from each origin point, and designating, for each origin point, whether the first path or the second path is preferable based on the probabilistic model.

In one embodiment, the set of origin points are arranged in a grid. In one embodiment, the first stroke center and the second stroke center are each of a type selected from a primary stroke center, a comprehensive stroke center, a primary plus stroke center, a thrombectomy capable stroke center, or an acute stroke ready hospital In one embodiment, the type of the first stroke center is different from the type of the second stroke center. In one embodiment, the first stroke center is a primary stroke center and the second stroke center is a comprehensive stroke center.

In one embodiment, at least one simulated infarct core growth model along the first path includes simulation of cerebrovascular imaging of the patient and simulation of administering intravenous tissue plasminogen activator to the patient. In one embodiment, the at least one simulated infarct core growth model along the first path further includes determining whether the simulated patient has a large vessel occlusion, and proceeding to the second stroke center if the large vessel occlusion is identified. In one embodiment, the parameters are selected from the initial infarct core volume, the total volume of at-risk tissue encompassed by the ischemic penumbra, or the collateral-dependent time constant. In one embodiment, the simulated infarct core growth models are generated via Monte Carlo simulations.

In one embodiment, the set of parameters comprises at least one patient-specific parameter selected from patient age, race, gender, height, weight, suspected time since stroke onset, or comorbidities. In one embodiment, the set of parameters comprises at least one environmental parameter selected from time of day, traffic conditions, demographic/census data in the vicinity of the patient starting point, or hospital waiting time. In one embodiment, the method further comprises modifying at least one range of at least one parameter of the set of parameters based on additional information collected specific to a patient. In one embodiment, the method further comprises recalculating the probabilistic model of patient outcomes from the patient starting point using the modified parameters.

In one embodiment, the method further comprises modifying at least one range of at least one parameter of the set of parameters based on additional information specific to a stroke network. In one embodiment, the method further comprises modifying at least one range of at least one parameter of the set of parameters based on additional information specific to an area in a vicinity of the patient starting point. In one embodiment, the method further comprises transmitting the destination of the designated path and an estimated time of arrival to a database.

In one aspect, a system for displaying a desired transport route for a stroke patient comprises a computing device communicatively connected to a GPS receiver, and having a non-transitory computer-readable medium with instructions stored thereon, which when executed by a processor perform steps comprising receiving, from the GPS receiver, a starting point, generating a set of simulated infarct core growth models for simulated stroke patients along at least a first path to a first stroke center followed by an optional trip to second stroke center, and a second path directly to the second stroke center, including querying travel time under current traffic and weather conditions along the first and second paths, varying a set of parameters of the simulated stroke patients across the set of simulated infarct core growth models, calculating a probabilistic model of patient outcomes from the set of simulated infarct core growth models from the patient starting point, and designating whether the first path or the second path is preferable based on the probabilistic model.

In one embodiment, the steps further comprise selecting a closest origin point to the origin position from a database of origin points, querying a desired transport route for a stroke patient from the database, corresponding to the closest origin point, displaying, on a display, a desired transport route for a stroke patient from the closest origin point, and periodically updating the database of origin points by performing steps comprising: from each origin point of the database of origin points, generating a set of simulated infarct core growth models for simulated stroke patients along at least a first path to a primary stroke center followed by an optional trip to a comprehensive stroke center, and a second path directly to the comprehensive stroke center, including querying travel time under current traffic and weather conditions along the first and second paths, varying a set of parameters of the simulated stroke patients across the set of simulated infarct core growth models, calculating a probabilistic model of patient outcomes from the set of simulated infarct core growth models from each origin point, and designating, for each origin point, whether the first path or the second path is preferable based on the probabilistic model.

In one embodiment, the system further comprises at least one remote computing device communicatively connected to the computing device, and comprising a non-transitory computer-readable medium comprising the database. In one embodiment, the steps further comprise modifying at least one range of at least one parameter of the set of parameters based on additional information collected specific to the stroke patient.

In one embodiment, the steps further comprise recalculating the probabilistic model of patient outcomes from the patient starting point using the modified parameters. In one embodiment, the system further comprises at least one sensor communicatively connected to the computing device and configured to record data related to the patient, the computing device further configured to receive the data from the sensor. In one embodiment, the sensor is selected from a sound sensor, a temperature sensor, a pressure sensor, or an ambient light sensor.

In one embodiment, the steps further comprise displaying the data received from the sensor on the display. In one embodiment, the computing device is a smartphone, a laptop, or a tablet. In one embodiment, the system further comprises a vehicle, the vehicle comprising the computing device.

In one aspect, a method of calculating a preferred location for a mobile treatment unit in a geographic region comprises obtaining a weighted graph representation of a road network in a geographic region, comprising a set of weighted nodes corresponding to intersections in the road network and a set of weighted edges corresponding to connecting roads between the nodes, adjusting a weight of at least one node based on a calculated stroke risk at or near the corresponding intersection, calculating a closeness centrality of one or more nodes in the weighted graph, and selecting at least one node of the one or more nodes in the weighted graph having the smallest closeness centrality as a preferred location for a mobile treatment unit.

In one embodiment, the mobile treatment unit is a mobile stroke treatment unit. In one embodiment, the method further comprises the steps of obtaining traffic information for one or more roads in the geographic region, adjusting at least one weight of the set of weighted edges to account for expected additional travel time on the corresponding road due to increased traffic; and recalculating the closeness centrality of one or more nodes in the weighted graph. In one embodiment, the at least one node comprises a plurality of nodes, corresponding to a plurality of mobile treatment units; and further comprising the steps of receiving a communication that one of the plurality of mobile treatment units is unavailable, recalculating the closeness centrality of the plurality of nodes in the weighted graph, and selecting at least one different node of the plurality of nodes in the weighted graph to redeploy the remaining mobile treatment units of the plurality of mobile treatment units.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 8A depicts the Mothership (MS) simulations and FIG. 8B depicts the Drip and Ship (DNS) simulations. Monte Carlo methods generate a population of patients with LVOs and non-LVOs. The time taken from stroke onset to successful reperfusion from treatment determines how much of a patient's penumbra volume their infarct core achieves (Equation 3, as shown in the Experimental Examples below). An LVO patient has a probability of successful reperfusion from EVT (green) at the CSC, or from tPA (purple) at the PSC. A non-LVO patient has a probability of successful reperfusion from tPA (purple) at either stroke center. Those that do not successfully reperfuse from any treatment (grey) have a final infarct core volume that is equal to their ischemic penumbra. For nodes with exceptionally long transport times, the final infarct core volume could be approximately equal to the penumbra volume despite successful reperfusion from treatment. For a given transport strategy simulation, the distributions of final infarct core volumes of non-LVO and LVO patients were aggregated and then translated to a distribution of 90-day mRS via Equation 6, as shown in the Experimental Examples below. For visualization purposes, the proportions of green, purple, and grey are not exactly to scale with the values presented in Table 2, as shown in the Experimental Examples below. The illustrated patient populations on the left-hand side are not representative of the 25/75 stroke type distribution for the same reason.

DETAILED DESCRIPTION

Figure 1:
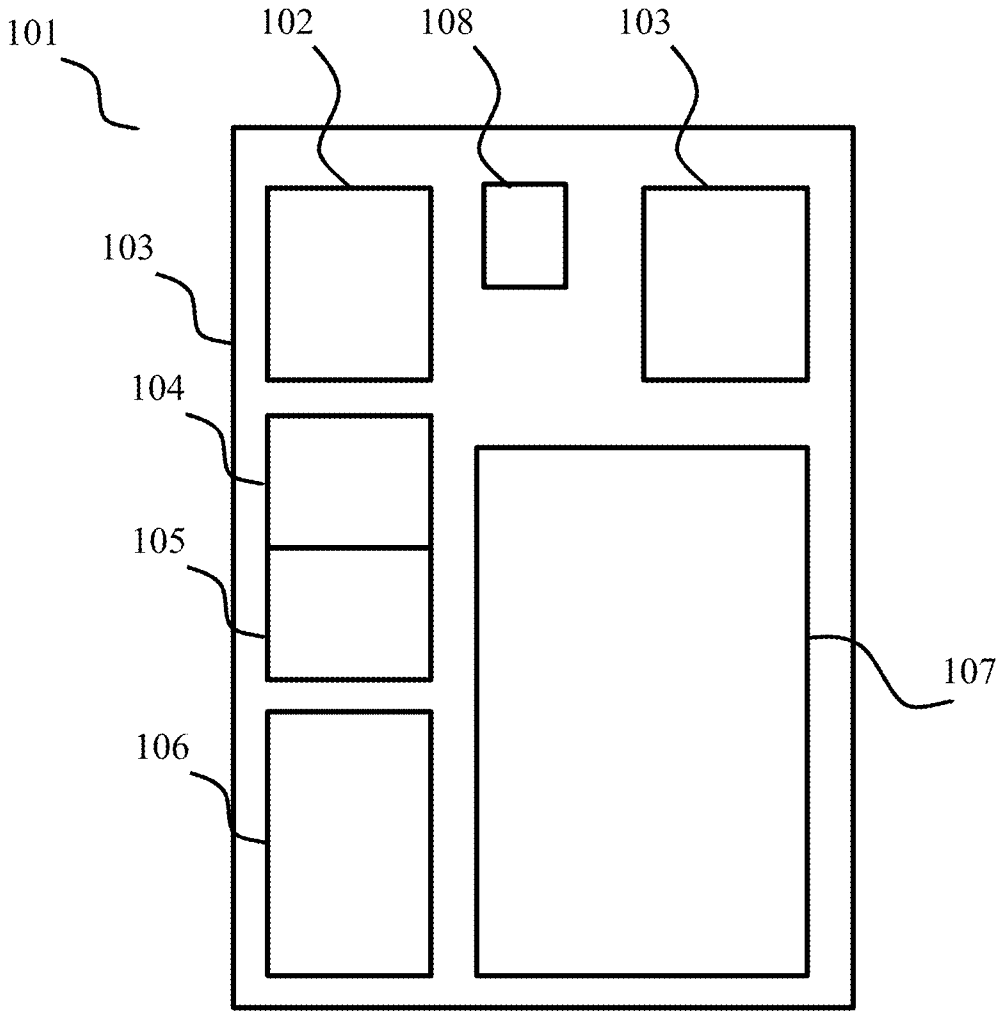
FIG. 1 is an exemplary portable computing device of the disclosure.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C #, Objective-C, Java, JavaScript, MATLAB, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Disclosed herein is a novel framework that uses a physiological model of time-dependent infarct core growth and represents key, patient-specific parameters as population-based distributions. These applications focus on improvement of EMS transport decisions and regional bypass policies. In certain aspects, the present invention relates to systems, devices, and methods for making or aiding transport decisions for a subject who had, or who is having, a stroke.

In one embodiment, a framework as disclosed herein comprises an algorithmic selection among a set of destinations and transport strategies for a stroke patient based on a readily available set of inputs, including but not limited to the starting point (patient pick-up point), demographic information about the stroke patient (including but not limited to race, age, weight, sex), stroke risk factors (e.g. hypertension, diabetes cholesterol, smoking, and other comorbidities), one or more stroke severity scales, the approximate time of stroke onset, the last known well time, interventionalist time delay, collateral flow (measured in the field in some embodiments, atrial fibrillation, known medication use, for example existing anticoagulant use, baseline (pre-stroke) modified Rankin Scale, number of simultaneous emergency stroke calls within a specified time window, etc.

In some embodiments, a system or method may further take into account other readily available information not specific to the patient, for example time of day, traffic conditions, demographic/census data in the vicinity of the starting point, and/or hospital waiting time. In some embodiments, a system or method may take into account patient-specific data or distributions, for example any or all of the demographic and/or stroke risk factor data elements discussed here, based on the demographic/census data in the vicinity of the starting point. For example, instead of or in addition to any known data specific to the stroke patient being transported, a system or method herein may use as an input to a statistical model any available statistical distributions of data known about the population local to the starting point, based on available census or demographic data.

In some embodiments, a system or method may comprise the construction of a map, heat map, lookup table, or other static or dynamic representation of a suggested transport strategy for a generic stroke patient from one or more of a set of starting points, for example a set of starting points arranged in various locations around a region or metropolitan area. In one embodiment, a transport strategy is selected from one of two destination points (a PSC or a CSC) with a further trip to a CSC from the PSC if an LVO is identified. In other embodiments, a model may include multiple PSCs and/or CSCs, and so the list of possible transport routes may comprise any of the list of CSCs, plus any of the list of PSCs with a further trip from each PSC to each of the possible CSCs. In some embodiments, geographic circumstances may mean that certain of the maximum possible routes are never practical from any starting point. Similarly, certain starting points may be naturally limited to a smaller subset of the possible transport routes by their location.

Although certain embodiments are disclosed herein with reference to one or more different types of stroke center or care facility (for example a primary stroke center and a comprehensive stroke center), it is understood that the methods and systems disclosed herein may be used in some embodiments to calculate and/or choose routes to and from any suitable care facility or stroke center, including but not limited to a primary stroke center, a comprehensive stroke center, a primary plus stroke center, a thrombectomy capable stroke center, or an acute stroke ready hospital.

In some embodiments, the starting points are arranged roughly in a grid, with a certain average distance between points in two orthogonal directions (for example East-West and North-South). In some embodiments, the average distance may be 100 meters, 200 meters, 500 meters, 1 kilometer, 2 kilometers, or 5 kilometers. In some embodiments, starting points may be arranged in another configuration more fitting to the natural layout of the streets of a region, for example according to a block grid. Systems and methods of the invention may then include rounding an actual starting point (for example as determined by GPS, street address, and/or cellular triangulation) to the nearest starting point from the set of starting points.

In one aspect, the present disclosure relates to a device, for example a portable computing device 101 as shown schematically in FIG. 1. Computing device 101 may include one or more sensors or transceivers configured to calculate a location of the computing device, for example a GPS or other location system receiver 102 and a cellular, Wi-Fi, and/or Bluetooth transceiver 103. Transceiver 103 may be configured for one- or two-way communication with one or more remote systems or users via any communication format known in the art, and/or may be further configured to provide coarse or fine location information, for example via Wi-Fi or cellular fingerprinting, base station triangulation, or the like.

In some embodiments, computing device 101 comprises at least one processor 104 and a non-transitory computer-readable medium 105. The non-transitory medium 105 may comprise software instructions executable on the processor 104, and may also include data, for example calculated mapping data or coordinate data as discussed herein for use by a software, for example the disclosed instructions, in performing methods of the disclosure. In some embodiments, computing device 101 may further comprise one or more sensors 106, which may include any sensors known in the art, for example sound sensors (e.g. microphones) temperature sensors, ambient light sensors, pressure sensors, or the like. Computing device 101 may further comprise a display 107, which may be a touch screen display, for use as an output and/or input device for a software executing on a processor 104. The display may be for example an LCD or LED or OLED display.

Computing device 101 may further comprise one or more indicators 108, including for example speakers, indicator lights, buzzers, or the like, configured to provide visual or auditory feedback for example from a software executing on the processor 104. In some embodiments, communication transceiver 103 may comprise a Wi-Fi, Bluetooth, Zigbee, or other short-range communication transceiver and the device 101 may be communicatively connected via the transceiver to one or more patient monitoring devices, for example in an ambulance. Suitable patient monitoring devices include, but are not limited to, a pulse/ox meter, a blood pressure monitor, an electrocardiogram (EKG or ECG), a transcranial doppler (TCD) ultrasound, for example to measure collateral flow, a portable CT scanner, a near-infrared spectroscopy (NIRS) instrument, a functional near-infrared spectroscopy (fNIRS) instrument, etc. Computing device 101 may further include a housing 103 enclosing all or some of the components shown in FIG. 1.

In some embodiments, device 101 may include mapping and navigation software, for example configured to provide turn-by-turn navigation on display 107 based on a calculated location of device 101, and according to a calculated or received transport route. Device 101 may further include a user interface configured to show, for example turn-by-turn navigation, data measured from one or more sensors, data about one or more stroke patients, data about one or more care facilities, traffic data, digital dispatch information, dispatchers notes, a one- or two-way messaging interface with a dispatcher and/or care facility, or the like.

Figure 2:
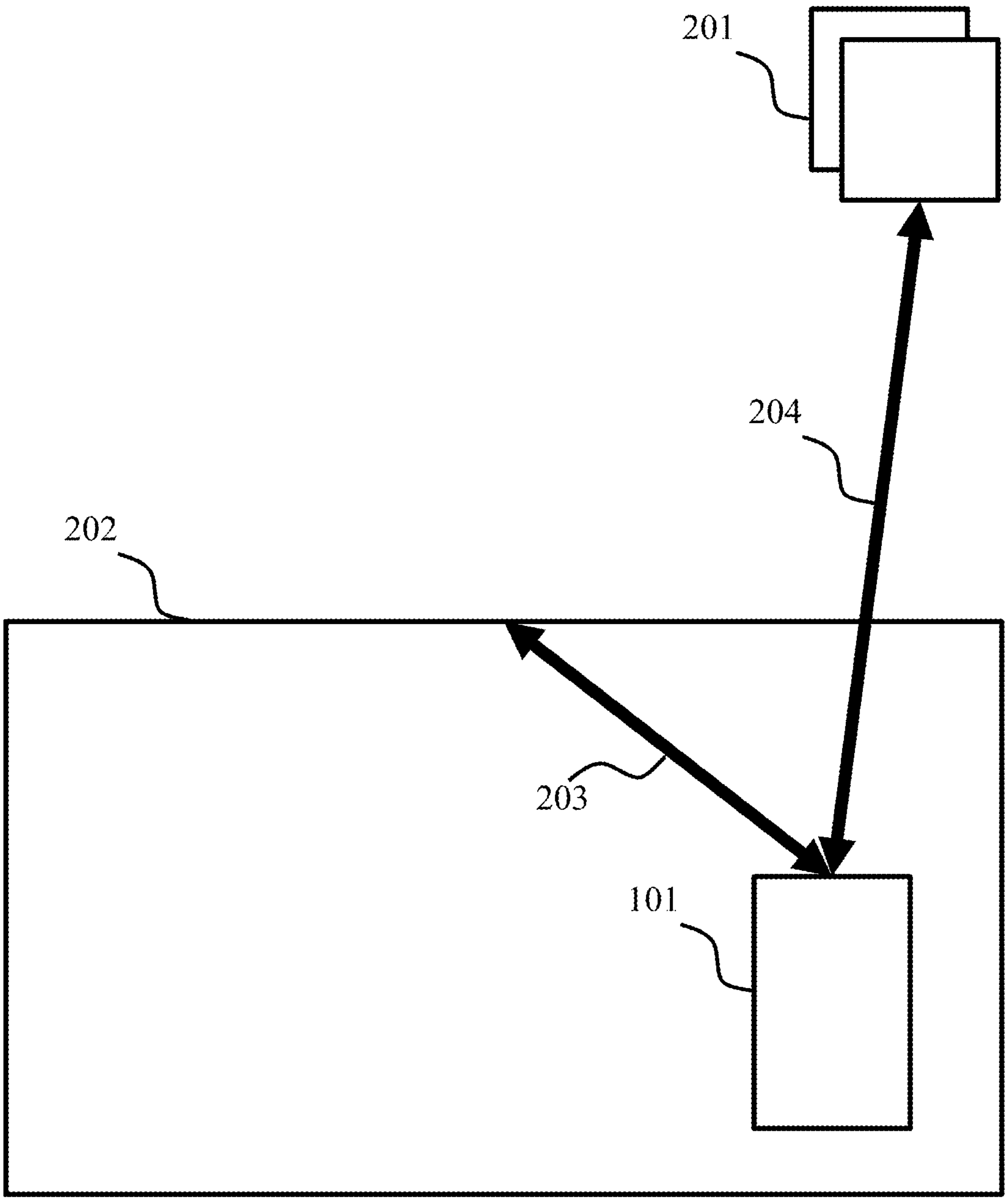
FIG. 2 is an exemplary system diagram of the disclosure.

In some embodiments a system of the disclosure comprises device 101 as disclosed in FIG. 1. In some embodiments, such as shown in FIG. 2, a system may comprise device 101 as part of a larger infrastructure, for example communicatively connected to a vehicle 202, for example an ambulance, via a link 203. Link 203 may comprise a wired and/or wireless communication link, for example a USB or Bluetooth connection, and may in some embodiments further comprise a connection to one or more instruments or devices positioned inside the vehicle or ambulance, for example configured to gather data about a patient riding in the ambulance or vehicle 202. Link 203 may further comprise wired or wireless charging capability for device 101, such that a battery or other power storage device (not shown) in device 101 is charged when the device 101 is connected to vehicle 202. The device 101 may further be communicatively connected to one or more remote computing devices 201, via link 204, which may use any wired or wireless communication protocol. Communication link 204 to remote computing devices 201 may be used for example to transmit data to be processed on remote computing devices 201, and to receive the results of any processing/calculations on device 101. For example, in one embodiment, a map of a region comprising a set of origin points may periodically recalculate the best transport route from each origin point based on traffic, weather, etc., and said calculations may be performed on remote computing devices 201. Then, when device 101 required a route from a given origin point, it could simply query the best path from remote computing device 201 via communication link 204. Remote computing device 201 may comprise one or more servers, or may also comprise cloud servers or virtual servers.

As disclosed herein, a "vehicle" includes anything used for transporting people or goods, including but not limited to an ambulance, a fire truck, an automobile, a van, a limousine, a helicopter, an airplane, a motorcycle, a bus, a minibus, a truck, a locomotive, a taxi, or any other suitable mode of transportation.

In some aspects as contemplated herein, device 101 is a dedicated, custom-built computing device comprising all sensors, communication transceivers, and software. In other embodiments, a commodity portable computing device, for example a smartphone, laptop, or tablet, may be used as device 101 with the software downloadable and installable, for example as an App.

In one aspect, a method of selecting a transport route is disclosed. The method may in some embodiments be a computer-implemented method, comprising instructions executed by a processor. Instructions may be executed by a processor on a portable device, on a remote computing device, or a combination of the two.

Figure 3:
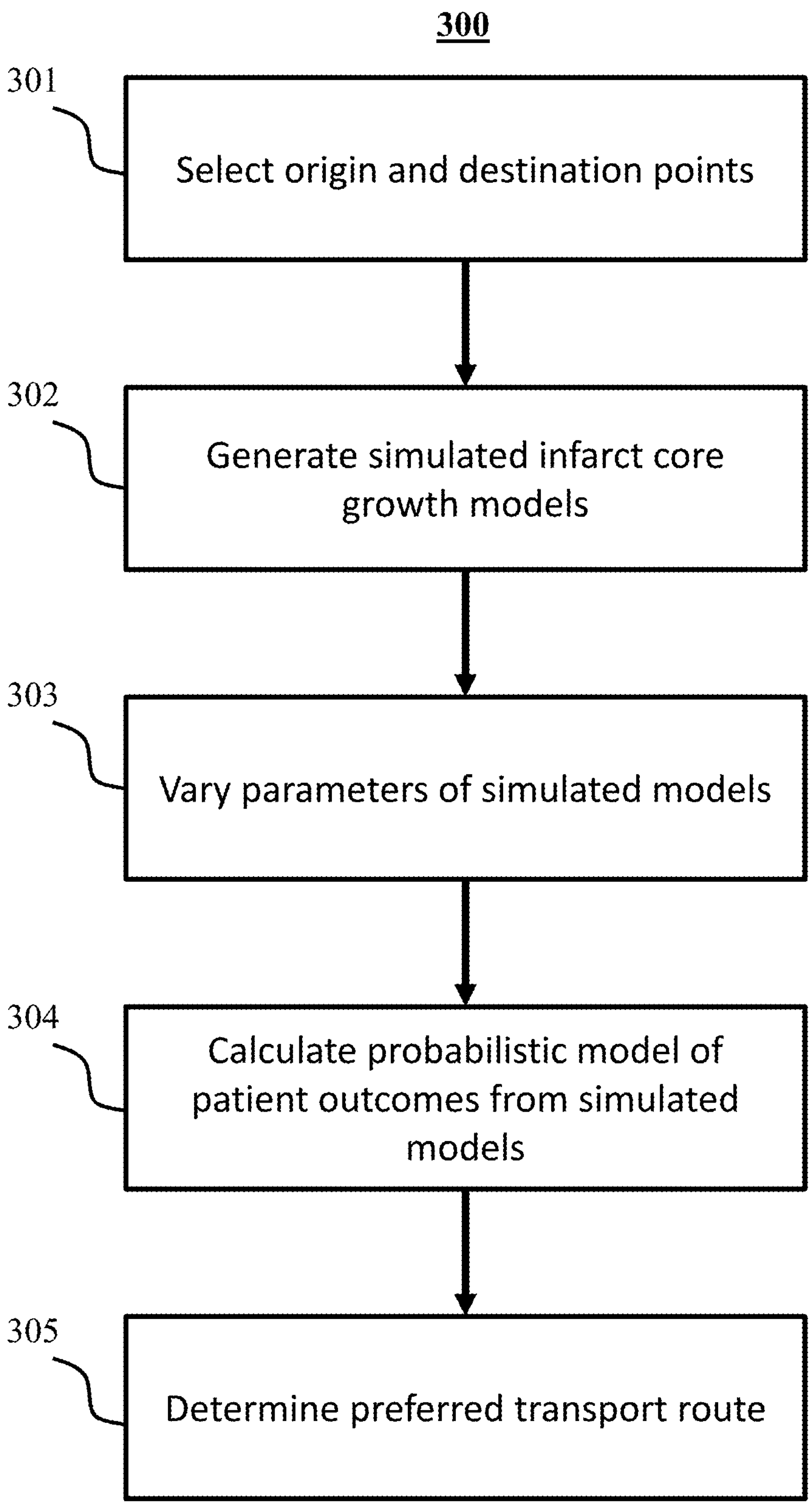
FIG. 3 is an exemplary method of calculating a set of desired transport routes.

One embodiment of a method disclosed herein is shown in FIG. 3. The method 300 includes the steps of selecting a set of origin points and a set of destination points, for example at least one primary stroke center and at least one comprehensive stroke center, in step 301, generating a set of simulated infarct core growth models from each origin point for simulated stroke patients along at least a first path to the primary stroke center followed by an optional trip to the comprehensive stroke center, and a second path directly to the comprehensive stroke center in step 302, varying a set of parameters of the simulated stroke patients across the set of simulated infarct core growth models in step 303, calculating a probabilistic model of patient outcomes from the set of simulated infarct core growth models from each origin point in step 304, and designating, for each origin point, whether the first path or the second path is preferable based on the probabilistic model in step 305.

In some embodiments disclosed herein, a method may comprise pre-calculating one or more simulated infarct growth models from a set of fixed origin points in a region. In some embodiments, additionally or alternatively to calculating simulated infarct growth models or preferred transport routes from the set of fixed origin points, a device or method may include the steps of calculating simulated infarct growth models on the fly from the exact starting point, i.e. the pickup location of the stroke patient in question. In this way, where sufficient computing resources are available, a system or method of the disclosure may determine the preferred transport route accurately for the stroke patient in question, from the exact pickup location.

Certain steps of methods disclosed herein may be executed periodically as background processes. In one example, one or more maps or sets of preferred transport routes may be updated periodically in the background, for example in response to changing traffic data, changing hospital wait time data, or the like. In one example, traffic and/or weather data may be updated periodically in the background, for example by querying one or more remote services and providing location information. In some embodiments, hospital or care facility wait time data may be updated periodically in the background, for example using an available application programming interface (API) or data service to query information from a hospital. In some embodiments, some or all of these data may be updated using projected or predicted values, for example hospital wait time data may be guessed based on historical data, weather, time of day, time of year, etc.

In some embodiments, a method includes receiving a call to pick up a patient from a location, for example a stroke patient. In some embodiments, a method may comprise certain steps which may be performed immediately after the call to pick up a patient is received. For example, a method may comprise the step of identifying the nearest origin point from a set of predetermined origin points to the pickup location. A method may comprise the step of updating traffic and weather information in the vicinity of the pickup location. A method may comprise the steps of calculating or querying the nearest PSC and/or CSC to the pickup location. In some embodiments, a method may query for or calculate the nearest two, three, four, or five PSCs and/or CSCs from a pickup location. In some embodiments, a method may comprise the step of querying the one or more PSC and/or CSC wait times, and/or updating traffic information in the vicinity of the one or more PSCs and/or CSCs. In some embodiments, a method may include the step of querying how busy or full one or more PSCs and/or CSCs are, for example in order to model various additional times needed to construct a stroke model for the patient, including but not limited to a door-to-needle time, a needle-to-door-out time, and a door-to-puncture time. These times may in some embodiments be calculated, predicted, or modeled based on real-time queried data about staffing, supplies, and traffic, or may in other embodiments be calculated, predicted, or modeled based on historical data and by drawing correlations from available environmental data (e.g. time of day, time of year, weather, traffic, etc.) Using all these data points, a method of the disclosure may comprise the step of beginning to calculate approximate transport times even before a patient has been picked up, in order to more quickly depart for the intended destination once the stroke patient has been secured in the vehicle.

In some embodiments, methods disclosed herein may comprise certain data acquisition and calculation steps performed at the time a stroke patient is picked up from the pickup location. For example, any environmental information, e.g. traffic, weather, that was acquired before pickup may be validated to ensure that it has not changed sufficiently to impact the calculated transport time model(s). In some embodiments, a method may comprise steps of recalculating one or more transport times or preferred transport routes.

Further steps which may be performed at the time a stroke patient is picked up include collecting or verifying any demographic or patient-specific information, including but not limited to patient age, race, gender, height, weight, suspected time since stroke onset, comorbidities, etc. In some embodiments, a method includes immediately departing along the calculated preferred transport route and adding the collected or verified demographic or patient-specific information in transit, while in other embodiments some data may be added or verified prior to departure. In some embodiments, a method may include the step of an EMT, clinician, or assistant removing a portable computing device of the disclosure from the vehicle and taking the portable computing device to the patient while the patient is being loaded onto a stretcher or gurney, so that some information can be added or verified prior to departure but without delaying departure.

In some embodiments, a user interface of the disclosure may automatically present some or all demographic or patient specific information to a clinician, EMT, or assistant on a display, for example on a display of a portable electronic device, so that the received data can be verified or missing data added in the presence of the patient in question.

In some embodiments, before or during transport, a method may comprise the step of calculating a mathematical model of infarct growth in a stroke patient based on collected or calculated data. Further details regarding exemplary calculations of infarct growth models are included in the Experimental Examples below. In some embodiments, infarct growth models may be calculated for a variety of estimated stroke onset times and a variety of time constants. In some embodiments, demographic or patient specific data may be used to select a subset or range of available time constants to use in calculating infarct growth models. In some embodiments, a method may comprise the step of further calculating a 90-day modified Rankin Score (mRS) based on the infarct growth models and one or more calculated transport times. In some embodiments, a threshold may be applied to the mRS, for example a threshold of 5 or 6. In some embodiments, multiple infarct growth models may be simulated and mRSes calculated from the multiple models, and the collected mRSes may be aggregated, for example for a given transport route, in order to determine a probabilistic model of mRS and/or patient outcome for a given transport route.

In some embodiments, before or during transport, a plurality of simulated patients may be used to calculate projected infarct growth models and mRSes from one or more starting points in a set of starting points on a map, for example a random set of simulated patients to construct a Monte Carlo simulation. In some embodiments, the parameters of the simulated patients in the Monte Carlo simulation may be varied or skewed based on individual patient-specific data (for example, if a patient has a known comorbidity) or based on demographic data in the vicinity of the pickup location (for example, if a high proportion of the population in the vicinity of the pickup location is known, for example based on census data, to be of a certain race or age). In this way the random distribution of outcomes can be tuned to more accurately reflect a valid probabilistic model of patient outcomes given available information.

The use of a Monte Carlo or other randomized statistical simulation to generate infarct growth models is advantageous over existing methods, which attempt to use clinical data sets to arrive at similar conclusions. By using randomized methods, the disclosed methods and systems can more accurately model infarct growth, for example by controlling how many of the random stroke models are LVO vs. non-LVO, or by merging known demographic information about a starting point (e.g. age, race, gender) into the randomized statistical simulation, so that the random stroke models more accurately reflect the likely patient population in the vicinity of a given starting point. Monte Carlo simulation also allows for finer control over the parametrization of, for example, the infarct growth time constant, which in turn provides a more accurate picture of infarct growth rate across given populations. More generally, the use of random simulations allows for a data set to be generated from parameters that hew more closely to known values and ranges from literature and/or from the relevant local or regional population, instead of relying on potentially skewed distributions generated from clinical data that may be generated from a population statistically unrelated to the relevant population.

In addition to or alternative to generating randomized infarct growth models, as contemplated herein, a Monte Carlo or other statistical simulation may also be used to vary other parts of the system, for example any part(s) or aspect(s) of the model for which a statistical distribution is known. For example, in various embodiments, Monte Carlo or other statistical simulations may be used to vary hospital wait times, (for example onset to departure from pickup location with EMS ($t_{OTD}$); door-to-needle ($t_{DTN}$); needle-to-door-out ($t_{NTDO}$); expedited door-to-puncture ($t_{EDTP}$); door-to-puncture ($t_{DTP}$). Transport time to PSC ($t_{PSC}$); transport time to CSC ($t_{CSC}$); transfer time from PSC to CSC ($t_{PSC\text{-}CSC}$)) or traffic. In various embodiments, the distributions used may be actual known distributions available from observations or care facilities, or may alternatively be distributions calculated based on other factors, for example similar distributions in similar care facilities for hospital times, or similar distributions for traffic in similar regions.

In some embodiments, the parameters or ranges/alternatives for the various parameters used in a randomized statistical simulation may be determined based on known statistics or data, for example from a particular stroke network. As used herein, a "stroke network" is a network of hospitals or care facilities in a particular geographic area, for example in a metropolitan area. In some embodiments, a stroke network further comprises one or more of: patient transportation methods, for example EMS, ambulance providers, fire stations; transport pathways, including roads or other transportation infrastructure; etc. In some embodiments, a stroke network is defined as a service area of one or more EMS providers. In this way, the randomized statistical simulation may be tuned to match the general demographics or characteristics of the population of a given region, which may differ from larger averages, for example statewide, nationwide, or international averages. Generating random infarct growth models in this way provides advantages over existing methods using clinical data gathered from sources that may be far away and thus demographically different than the expected patient community in a region.

In some embodiments, parameters that may be varied according to a set distribution in a randomized model include, but are not limited to, stroke type (LVO vs. non-LVO), degree of collateral flow (in LVO), stroke volumes, modified Rankin scores, door-to-needle times, door-in-door-out times, door-thrombectomy times, demographic information including age, race, and/or sex, and various stroke risk factors or comorbidities. Risk factors include, but are not limited to, hypertension, diabetes, cholesterol level, smoking, or atrial fibrillation. In various embodiments, some or all of these parameters may be assigned probability distributions and the distributions may be used as inputs to a randomized statistical model to generate random infarct growth models for a given population.

In some embodiments, a method may comprise selecting from one of a fixed number of possible transport routes. In some examples, at the time a patient is picked up, the probability of a good patient outcome along a first DNS route and a second MS route may be close, or within a certain threshold, for example 5%, 10%, 15%, or 20%. In some such examples, a method may comprise the step of comparing the two transport routes to identify common path elements at the start of the transport route, for example turns to leave a subdivision or property development, or turns shared among routes to a PSC and a CSC that are generally in the same direction from the pickup location. In such embodiments, a method may comprise the step of identifying a latest divergence point between or among the two or more possible transport routes, and delaying the selection of a preferred transport route until the vehicle containing the patient has reached a point closer to the latest divergence point. For example, one scenario may involve selecting between a DNS transport strategy first stopping at a PSC accessible from a first exit on a highway, and a second MS transport strategy instead driving straight to a CSC accessible from a further, second exit from the same highway. In this scenario, the first exit on the highway is the latest divergence point, because taking the first exit would lead the vehicle to the first transport strategy and the PSC, while remaining on the highway and not taking the first exit would lead the vehicle to the second transport strategy and the CSC. The additional time for selection can allow EMTs, clinicians, or assistants to gather additional data from the patient in transit, or may in some embodiments allow for the collection of updated traffic, weather, hospital wait, or other environmental data.

In some embodiments, a method may include selection between two transport strategies whose projected outcomes do not differ or differ only insignificantly. In such embodiments, some methods may include a default selection when a statistical difference in outcomes is below a certain threshold (for example less than 10%, less than 8%, less than 5%, less than 3%, less than 2%, or less than 1%). In some embodiments, a default selection may be a MS transport route over a DNS transport route, but in other embodiments the DNS transport route may be the default.

In some embodiments, a disclosed method may additionally comprise steps of gathering additional data to improve the accuracy of future calculations and predictions. For example, a method may comprise the steps of recording actual travel time along a particular route to the initially calculated travel time. As the quantity of such historical data grows, calculated travel times can be improved by modifying calculations, for example calculations received via third-party services, to compensate for real-world circumstances. In another embodiment, a method may include the step of recording the time from arrival of the vehicle at the patient pickup point to departure, recording door-to-needle, door-to-door-out, and door-to-puncture times at various care facilities at various levels of traffic/staffing and at various times of day, so that in the future, received data related to hospital traffic and staffing can more accurately be translated into a total travel time, and in turn into a more accurate infarct growth model.

In some embodiments, a disclosed method may additionally comprise collaborative steps, for example interfacing with other like systems in the same geographical area to approximate not only the current wait time at a particular stroke center, hospital, or facility, but also receive basic, anonymized information about any other stroke patients that may be arriving at the same facility before the patient in question. Such additional intervening patients could burden resources or increase triage time at particular facilities, and may lead to a change in transport decision.

Figure 17:
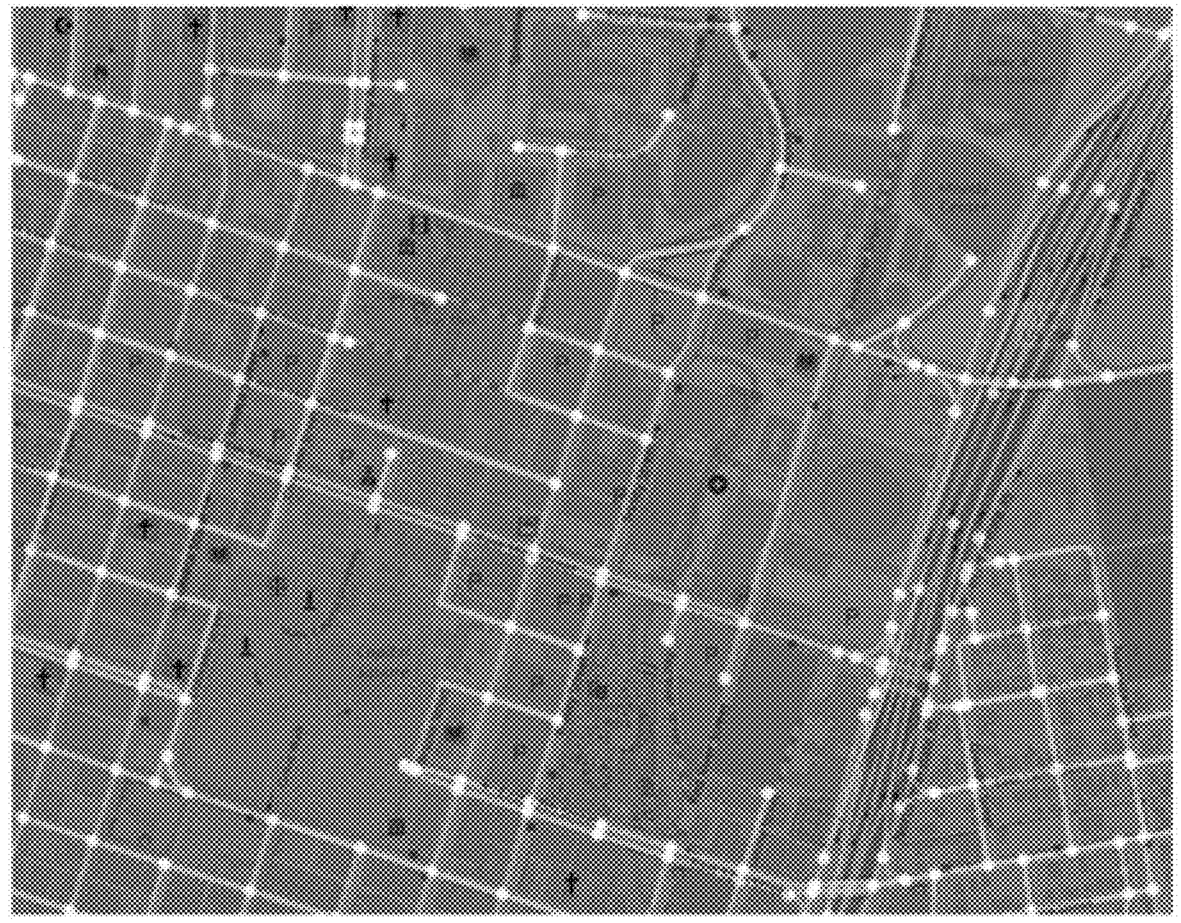
FIG. 17 depicts a map as a mathematical graph where each intersection is a node connected by roads.

In one aspect, a method for evaluating optimal mobile stroke unit home base placement using graph theory is disclosed. In another aspect, a method for evaluating optimal mobile stroke unit placement using graph theory is disclosed. In some embodiments, a road network is represented as a mathematical graph, where each intersection is a node, and the nodes are connected by the roads. Now referring to FIG. 17, shown is an urban city map with roads and intersections, wherein each intersection is a node, and the nodes are connected by the roads. In some embodiments, regional demographic data including, but not limited to, population distribution, population density, and population age are used to assign one or more of the nodes with a risk severity weighting. In some embodiments, regional demographic data can be sourced from census data to determine the stroke risk for each node. In some embodiments, historical data of stroke emergency calls are used to calculate the probability of where a stroke is likely to come from.

In some embodiments, the optimization of mobile stroke unit home base placement using graph theory is performed using a physiological model of stroke growth and minimization of travel time from the mobile stroke unit home base to the patient's location. In one embodiment, a metric called closeness centrality measures how close (the average shortest path length) a node is to all other nodes in the network. In one embodiment, the nodes with the smallest closeness centrality will represent the locations of the mobile stroke unit's home bases that are closest to all other points in the road network. In one embodiment, the calculation of "shortest path length" is computed using travel times as opposed to distances. In some embodiments, the calculation of "shortest path length" may be different at various times of day due to traffic patterns e.g. during rush hour vs during the middle of the night. In some embodiments, "shortest path length" is recalculated periodically for large networks and real time-updates of where mobile stroke units should stay are provided to the mobile stroke units.

In some embodiments, the closeness centrality metric identifies one or more optimal mobile stroke unit home bases. In some embodiments, the algorithm for identifying the optimal mobile stroke unit home base(s) from more than one location will change in order to include clustering analysis to subdivide networks into smaller subunits, each subunit governed by its respective single mobile stroke unit. In some embodiments, a sub-unit's respective area will change or shift as a result of a mobile stroke unit being called to a patient and being temporarily out of service for any new calls. In some embodiments, a real-time coordinating system is configured to collect location data from a plurality of mobile stroke units and further configured to account for mobile stroke units that are temporarily out of service. The real-time coordinating system may in some embodiments adjust the optimal location of remaining mobile stroke units given the change in coverage.

In one aspect, a method of finding a closed-form expression for the probability of a positive outcome for an LVO patient depending on the given transport strategy is disclosed. In some embodiments, the method comprises representing the infarct core volume as a transformation of random variables representing penumbra volume and noise from a distribution function. In some embodiments, a system of transformations is defined and then approximated using a Taylor Series expansion. In some embodiments, a first order approximation of the Taylor Series, followed by a determinant of a Jacobian matrix and integration of the equation therein recovers the desired marginal density. In various embodiments of the systems and methods disclosed elsewhere herein, examples are presented wherein Monte Carlo or other simulation models are used to generate simulated infarct core growth models for use in selecting transport routes and/or destinations for a subject. It is understood that the various systems and methods disclosed herein could interchangeably use a closed-form approximation of infarct core growth to calculate a probability of a positive outcome.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the system and method of the present invention. The following working examples therefore, specifically point out the exemplary embodiments of the present invention, and are not to be construed as limiting in any way the remainder of the disclosure.

Example 1: Optimizing Emergency Stroke Transport Strategies Using Physiological Models The criteria for choosing between Drip and Ship (DNS) and Mothership (MS) transport strategies in emergency stroke care is widely debated. While existing data-driven probability models can inform transport decision-making at an epidemiological level, herein a novel framework that uses a physiological model of time-dependent infarct core growth was developed and represents key, patient-specific parameters as population-based distributions. This framework was further implemented in two case studies to provide insight into how physiology can influence and potentially inform emergency stroke transport decisions. These applications focus on the optimization of EMS transport decisions and regional bypass policies in the Bastrop and Travis Counties in Texas. A detailed description of Texas stroke center capabilities and resources can be found in the Texas Department of State Health Services report.

Methods

Mathematical Model of Infarct Core Growth

If a stroke patient's ischemic region does not reperfuse, their infarct core will eventually attain the total ischemic penumbra volume. Mathematically, the physiology of a growing infarct core within the spatial constraint of its ischemic penumbra can be modeled as an exponential function.

Let $v(t)$ be the infarct core volume in mL at time t minutes after stroke onset, $v_p$ be the constant, total volume of at-risk tissue encompassed by the ischemic penumbra, and $\tau$ be the collateral-dependent time constant in minutes. The dynamics of the infarct core growth can be represented as the following differential equation, $$v_p = \tau\frac{dv(t)}{dt} + v(t) \quad \text{Equation 1}$$

which has the desired behavior for the instantaneous rate of change of infract core volume with respect to time, $$\lim_{v(t)\to v_p}\frac{dv(t)}{dt} = 0 \quad \text{Equation 2}$$

Suppose that there is no infarct volume at $t_0=0$ minutes after stroke onset, then $v(t_0)=0$. The solution to the given initial-value problem is then $$v(t) = v_p\cdot\left(1 - e^{-t/\tau}\right) \quad \text{Equation 3}$$

where the time constant $\tau$ determines the rate at which the infarct core volume $v(t)$ achieves the ischemic penumbra volume $v_p$.

Equation 3 has the desired behavior over a long timescale, $$\lim_{t\to\infty} v(t) = v_p \quad \text{Equation 4}$$

In the case of a patient with an LVO, an infarct core with poor collateral blood flow tends to grow faster and to a larger ischemic penumbra volume, while stronger collateral blood flow tends to slow infarct core growth and decrease the maximum ischemic penumbra volume.

The time constant $\tau$ was constructed to be parameterized by a 12-point pial collateral score (0-11), which is linearly dependent on large vessel ischemic penumbra volume in canines. The linear collateral-volume relationship was rescaled in canines to the scale of ischemic penumbra volumes found in human physiology using the two edge conditions: the mapping of the best collateral score with a minimum $v_p$ (pial=11, $v_p$=0 mL) and the worst collateral score with a maximum $v_p$ (pial=0, $v_p$=220 mL). Given these two points, the linear function $p(v_p)$ was constructed to relate pial collaterals and large vessel ischemic penumbra volumes in humans:

$$p(v_p) = (220 - v_p)\cdot\frac{11}{220} \quad \text{Equation 5}$$

The experimentally derived linear relationship between the rate-determining time constant $\tau$ and the pial collateral score p is then given by:

$$\tau(p) = (-0.0013\cdot p + 0.0179)\cdot 60 \quad \text{Equation 6}$$

Figure 4:
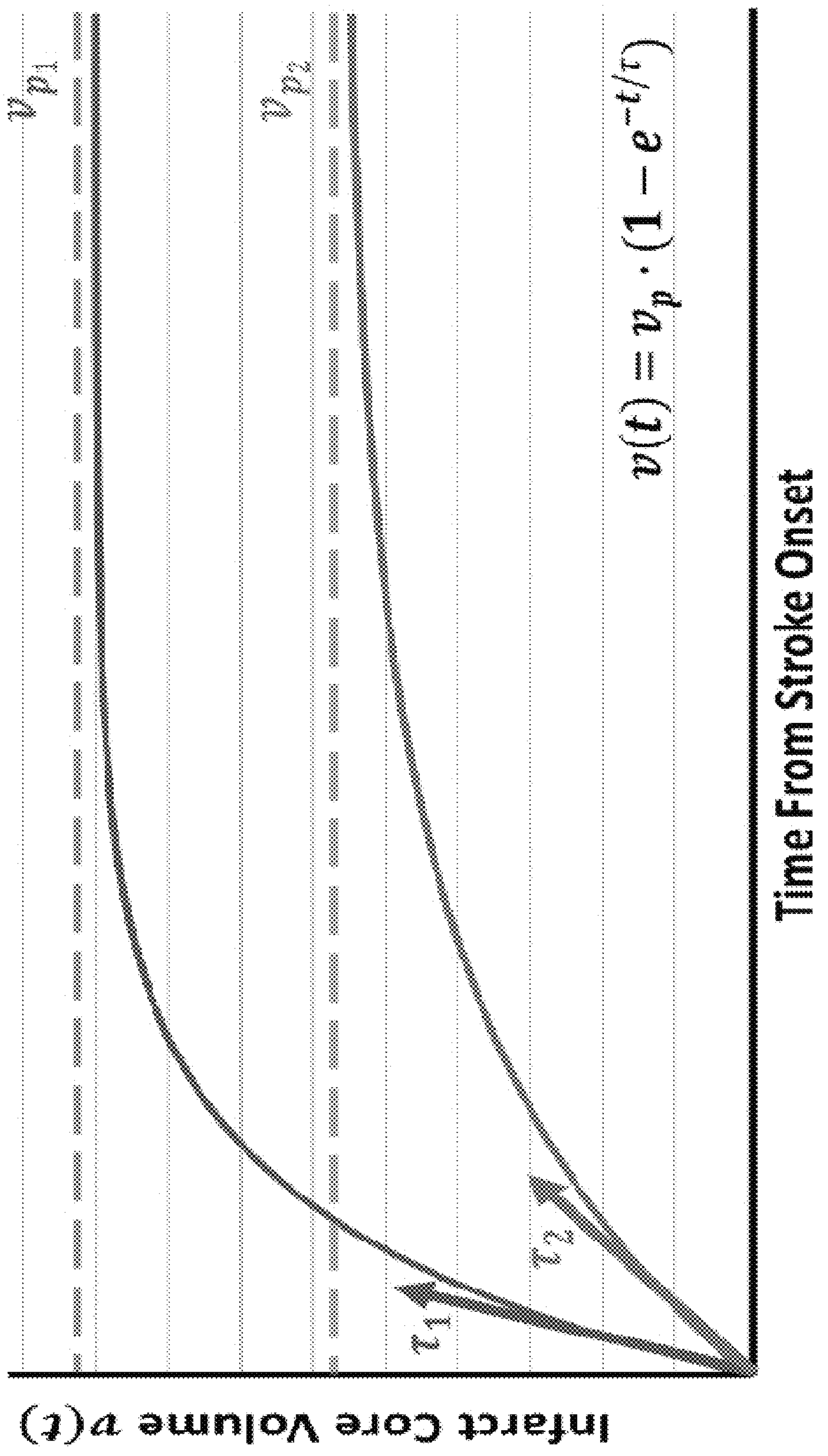
FIG. 4 depicts the visualization of Equation 3, as shown in the Experimental Examples below, the exponential function of infarct core volume. Each example curve corresponds to a single patient's infarct core volume over time, eventually reaching their ischemic penumbra volume $v_p$ if successful reperfusion is not achieved prior to full saturation. The time constant $\tau$, parameterized by patient-specific collateral blood flow, determines the rate at which the infarct core achieves its maximum value $v_p$. Because $\tau_1$ is steeper than $\tau_2$ (i.e. has a faster rate of growth), the red curve reaches $v_{p_1}$ sooner than the green curve reaches $v_{p_2}$.

FIG. 4 provides a visualization of the present exponential model of infarct core volume, which is consistent with existing experimentally and theoretically derived models.

It is important to note that the linear collateral-volume relationship should have associated uncertainty. Christiforidis et al provide the experimentally derived linear collateral-volume relationship, but do not provide confidence bounds. Future studies will expand this linear relationship to account for stochasticity in the random variables (i.e. a score of 11 is mapped to a distribution of possible ischemic penumbra volumes), contingent on the availability of relevant data. Nonetheless, this model allows one to expand these clinical variables to account for natural variation in patient-specific attributes.

Equation 3 was extended to relate infarct core volume to 90-day modified Rankin Score (mRS), a measure of patient outcomes, via the following linear function derived from Ernst et al's clinical study of outcome-volume association $$mRS(t) = 0.0376\cdot v(t) \quad \text{Equation 7}$$

and imposed the constraint that 90-day mRS cannot exceed an upper limit of 6, which represents patient death on the scale. Thus, Equation 7 allows one to compute a 90-day mRS outcome for any patient at time t after acute ischemic stroke onset. It is important to note that the disclosed framework uses a continuous scale of 90-day mRS outcomes because it provides a more mathematically sound basis for statistical testing and improves the accuracy of probability estimates.

EMS Transport Times

Figure 5:
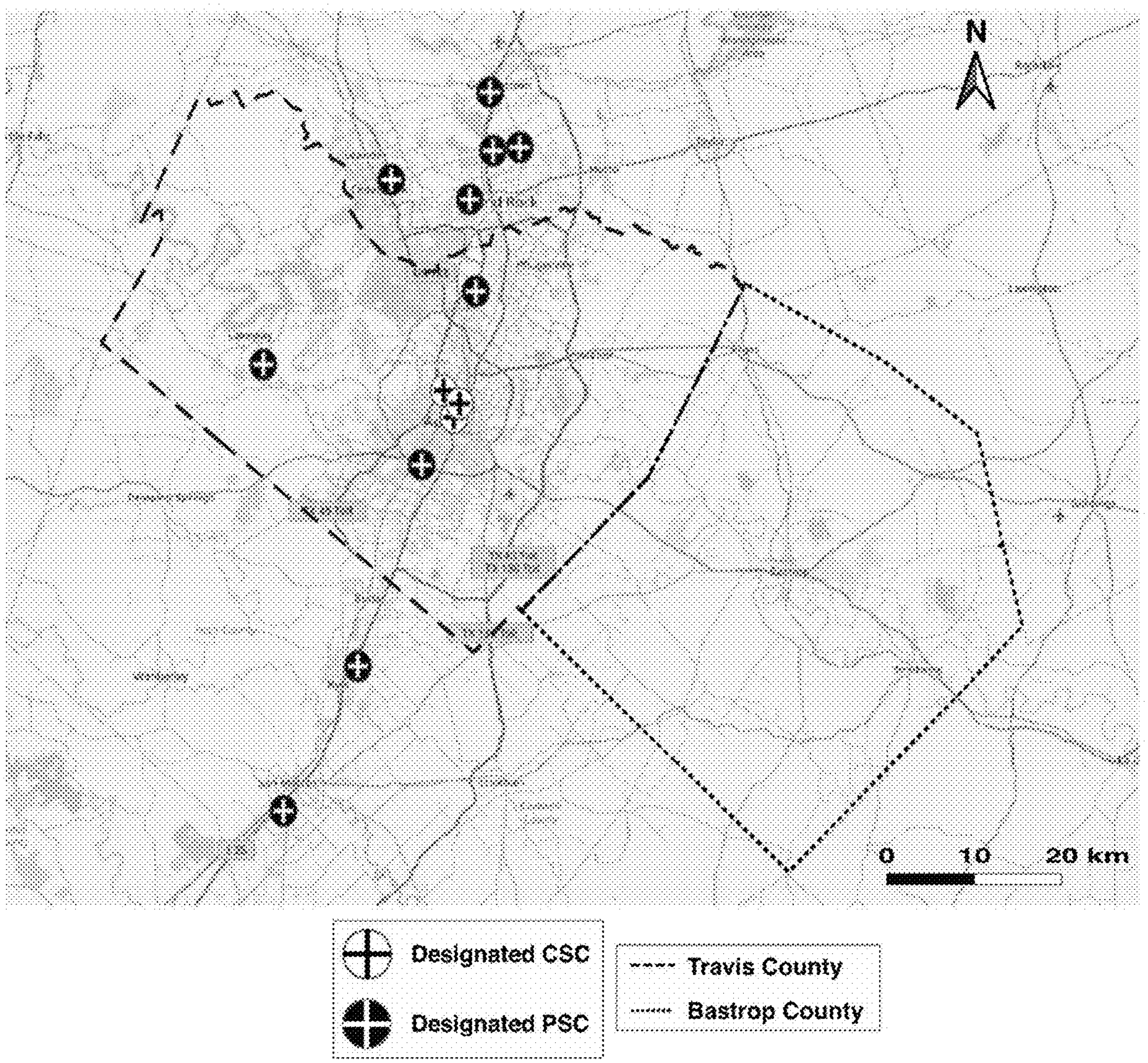
FIG. 5 depicts a map of Travis County (dashed outline) and Bastrop County (dotted outline). A coordinate grid consisting of hypothetical patient pickup locations is generated within the boundaries of each respective county. Stroke centers outside of these boundaries are still considered for emergency medical service (EMS) transport in the simulations.

The adjacent Travis and Bastrop Counties, Texas, are defined by the United States Census Bureau as urban and rural geographies, respectively. Their shared stroke network consists of three PSCs and three CSCs within Travis County, zero stroke centers within Bastrop County, and seven PSCs outside of both counties (FIG. 5). The following non-transport time intervals were assumed for this stroke network: stroke onset to departure from pickup location with EMS=60 minutes; door-to-needle (tPA)=30 minutes; needle-to-door-out=20 minutes; door-to-puncture (EVT) =30 minutes. Time intervals specific to a stroke center type were kept constant across the network, but hospital-level variation can be integrated easily with the provision of relevant data.

In order to compute EMS transport times in Travis County, Texas, a coordinate grid with 10,562 nodes spaced 500-meters apart was created, representing hypothetical patient pickup locations within the county. Of these nodes, 2,872 (27.2%) have a CSC as the nearest stroke center, so the optimal decision is clear. The focus of the present analysis was on the remaining 7,690 (72.8%) locations for which the optimal transport strategy is uncertain. An equivalently resolved coordinate grid was overlaid onto Bastrop County with 14,555 nodes, of which 11,959 (82.0%) were of interest in this analysis. Node-specific EMS transport times to the nearest PSC, nearest CSC, and transfer from the PSC to its nearest CSC were calculated with ArcGIS SDK (Esri, v10.8), utilizing average speed limits. Table 1, as shown below, provides transport time data averaged across the nodes of interest in each respective county.

TABLE 1

Mean transport time in minutes to the nearest PSC, nearest CSC, and transfer from the PSC to its nearest CSC.

| County | Time to nearest PSC | Time to nearest CSC | Transfer Time |
|---|---|---|---|
| Travis | 21.5 (SD = 11.3) | 29.5 (SD = 15.5) | 18.1 (SD = 10.1) |
| Bastrop | 39.8 (SD = 8.0) | 46.5 (SD = 8.8) | 30.8 (SD = 26.8) |

The total time for a DNS transport strategy is the sum of the time from stroke onset to departure from the pickup location, EMS transport time to the PSC, door-to-needle time, needle-to-door-out time, transport time to transfer from the PSC to its nearest CSC, and door-to-puncture time. A non-LVO patient on the DNS strategy does not proceed past the PSC. The total time for a MS transport strategy is the sum of the time from stroke onset to departure from the pickup location, EMS transport time to the CSC, and door-to-needle or door-to-puncture time depending on the stroke type.

Monte Carlo Patient Volume Generation

In lieu of a clinical dataset, Monte Carlo methods were used to generate synthetic data in order to model infarct core growth for a population of acute ischemic stroke patients. A notion of stochasticity was added to Equation 3 by letting $v_p$ be a beta($\alpha$, $\beta$) distributed random variable. Beta($\alpha$, $\beta$) distributions allow one to sample $n_{LVO}$=3,900 LVO and $n_{non\text{-}LVO}$=9,100 non-LVO $v_p$ values on a closed interval of realistically occurring ischemic penumbra volumes, [10 mL, 220 mL], unlike Gaussian distributions, for example. Furthermore, beta skewness was adjustable via the two shape parameters $\alpha$ and $\beta$, allowing one to characterize two independently generated distributions, one corresponding to a distribution of $v_p$ values representative of LVOs, and one corresponding to a distribution of $v_p$ values representative of non-LVOs. The LVO ischemic penumbra volume beta distribution has skew-left shape conditions ($\alpha$=2, $\beta$=2, generating the example distribution in FIG. 6A), and the non-LVO ischemic penumbra volume beta distribution has skew-right shape conditions ($\alpha$=2, $\beta$=6, giving FIG. 6B).

Administering EVT to an LVO patient with an onset-to-treatment time exceeding six hours is often inefficacious. At this point in time, it was supposed that the infarct core is essentially evolved to its asymptotic value $v_p$ and treatment administered thereafter would negligibly improve outcomes. Although the asymptote of the exponential growth model is never reached in finite time (a property of asymptotic models), it is known that at $t=5\tau$, $v(t)=0.9933\cdot v_p$, and it is at this point in time that the asymptotic value of the model was considered to be achieved. Accordingly, the median of the distribution of time constants outputted from Equation 6 were set corresponding to the beta distribution of $n_{LVO}$ penumbra volumes to be 1.2 hours.

Figure 6A:
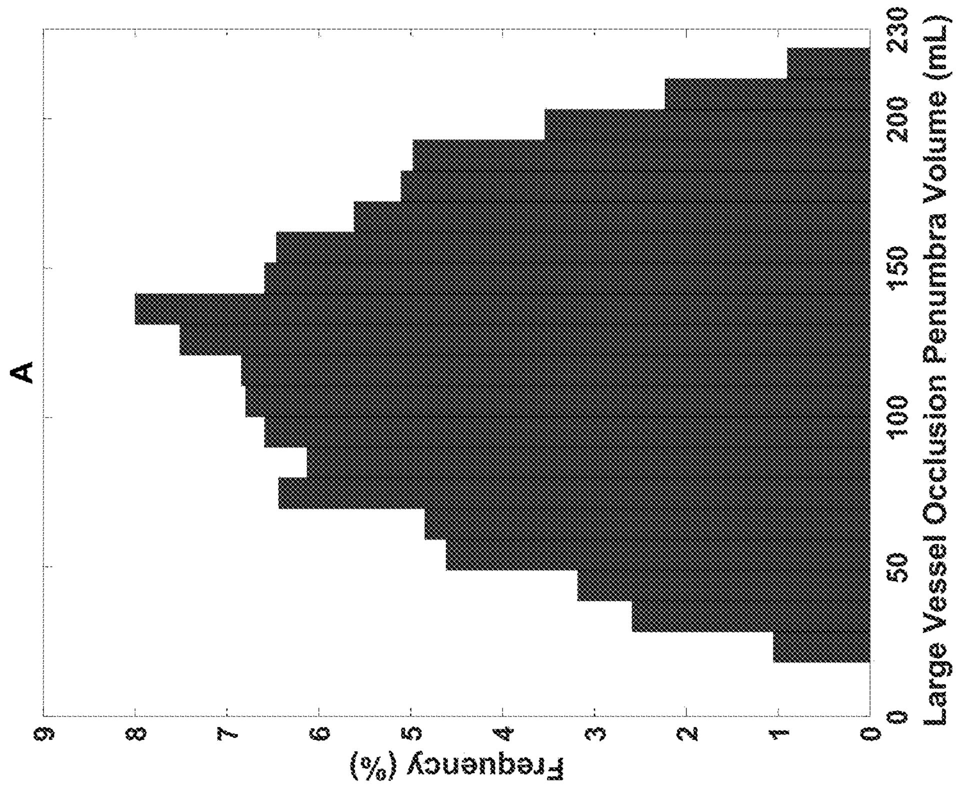
FIG. 6A and FIG. 6B depict exemplary results demonstrating distributions of Monte Carlo generated (FIG. 6A) LVO ischemic penumbra volumes ($n_{LVO}$=3900, mean: 115.2 mL, SD: 46.9 mL) and (FIG. 6B) non-LVO ischemic penumbra volumes ($n_{non\text{-}LVO}$=9100, mean: 69.9 mL, SD: 33.5 mL), sampled on the closed interval [10 mL, 220 mL]. These distributions are inputted into the time-dependent model of infarct core growth (Equation 3, as shown in the Experimental Examples below).
Figure 6B:
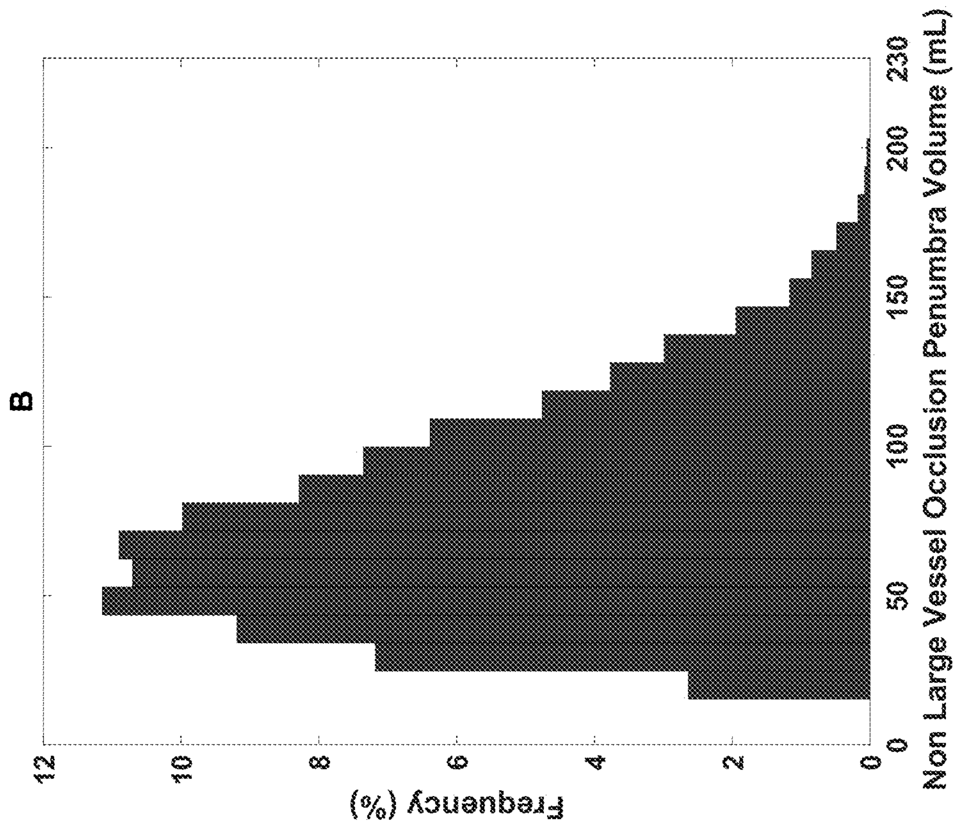

For every node of interest in the Travis and Bastrop Counties, 13,000 patients were simulated each with a randomly generated ischemic penumbra volume $v_p$. Of the total patients in each location, there were 3,900 LVO patients (25% incidence rate) with their $v_p$ sampled from a skew-left beta distribution, and 9,100 non-LVO patients (75% incidence rate) with their $v_p$ sampled from a skew-right beta distribution (FIG. 6A and FIG. 6B). The total number of patients simulated at each node of interest was chosen to maximize statistical power, thereby reducing Type II error, and to avoid unreliable significance testing that may result from oversampling or undersampling volumes.

The respective skewness of the generated LVO and non-LVO $v_p$ beta distributions were derived from published 90-day mRS outcome distributions for LVO and non-LVO patient subpopulations. The mean, range, and standard deviation of the LVO distribution resembles that of a sample of clinically measured LVO penumbra volumes. Moreover, while non-LVO volumes include a similar range of volumes related to LVO cases that spontaneously recanalize, there is a preponderance of smaller stroke volumes of lacunar infarcts caused by small vessel disease, further supporting the notion that non-LVO volumes tend to be skew-right.

Because Equation 3 was expanded to accommodate a distribution of ischemic penumbra volumes representative of a population of acute ischemic stroke patients, the collateral-dependent time constant $\tau$ also became a distribution for the LVO subpopulation. However, no literature has been identified that addresses the time constant $\tau$ parameterization with respect to non-LVO collateral blood flow. Therefore, for the non-LVO subpopulation, $\tau$ was varied and the results are presented using two extreme time constant parameterizations for non-LVO infarct core growth. In one case, $\tau$ was assumed to be the largest time constant (slowest rate of infarct core growth) from the distribution of LVO time constants, and in the second case t was assumed to be the smallest (fastest rate of infarct core growth). The generation of synthetic patient data and the following simulations were performed in MATLAB (MathWorks, version r2017b).

Emergency Stroke Transport Simulations

Figure 7:
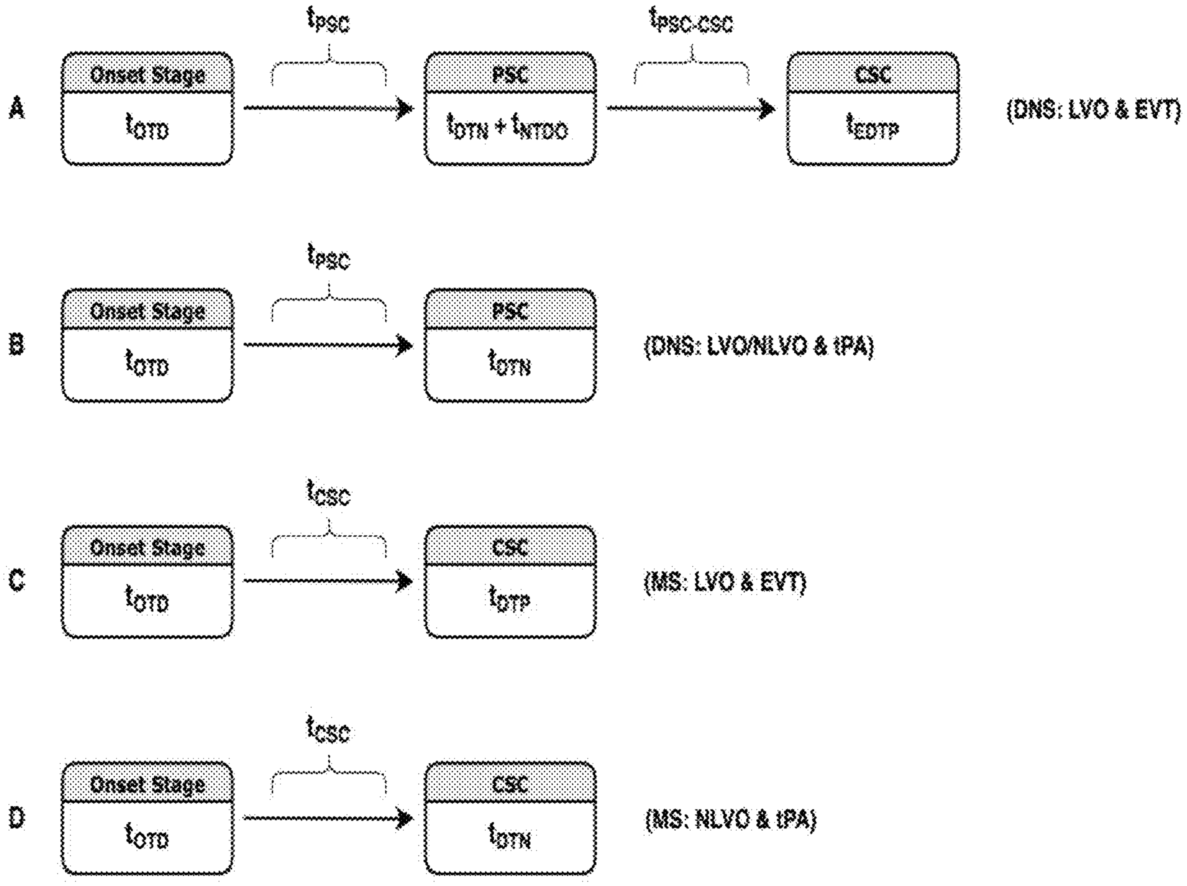
FIG. 7 depicts the four possible onset-to-treatment time pathways each consisting of pre-hospital, transport, and hospital time intervals. Pathway A shows the DNS pathway for a patient with an LVO that will reperfuse with EVT at the CSC. Pathway B shows the DNS pathway for non-LVO and LVO patients that will reperfuse with tPA at the PSC. Pathway C shows the MS pathway for LVO patients that will reperfuse with EVT at the CSC. Pathway D shows the MS pathway for non-LVO patients that will reperfuse with tPA at the CSC. The non-transport time intervals are defined in the presented model as: onset to departure from pickup location with EMS ($t_{OTD}$)=60 minutes; door-to-needle ($t_{DTN}$)=30 minutes; needle-to-door-out ($t_{NTDO}$)=20 minutes; expedited door-to-puncture ($t_{EDTP}$)=30 minutes; door-to-puncture ($t_{DTP}$)=30 minutes. Transport times vary by node: transport time to PSC ($t_{PSC}$); transport time to CSC ($t_{CSC}$); transfer time from PSC to CSC ($t_{PSC-CSC}$). Total time for each pathway: Pathway A ($t_{treatment|LVO,\ DNS,\ EVT}$)=140 minutes+$t_{PSC}$+$t_{PSC-CSC}$; Pathway B ($t_{treatment|LVO/non-LVO,\ DNS,\ tPA}$)=90 minutes+$t_{PSC}$; Pathway C ($t_{treatment|LVO,\ MS,\ EVT}$)=120 minutes+$t_{CSC}$; Pathway D ($t_{treatment|non-LVO,\ MS,\ tPA}$)=90 minutes+$t_{CSC}$. The DTN, DTP, and EDTP times are varied in the Sensitivity Analysis section below.

Timely acute stroke interventions can lead to successful reperfusion of the ischemic region, preventing the infarct core from expanding to the full ischemic penumbra volume. For patients that successfully reperfuse, their infarct core volume at the time of treatment is defined as the final infarct core volume. Final infarct core volume depends on the total elapsed time from stroke onset to successful reperfusion (Equation 3). A stroke patient can follow one of four possible onset-to-reperfusion time pathways, depending on their ischemic stroke type, transport strategy, and treatment (FIG. 7). Each pathway consists of non-transport time intervals and node-specific EMS transport times (transport time to the nearest PSC, nearest CSC, and transfer from the PSC to its nearest CSC). Those that do not successfully reperfuse from any treatment have a final infarct core volume that is equal to their ischemic penumbra volume.

For each node of interest in both counties, an emergency stroke transport scenario was simulated where the Monte Carlo generated stroke population (composed of 25% LVO patients and 75% non-LVO patients) followed the DNS strategy, and then the simulation was rerun with the MS strategy.

In the present simulations, it was assumed that administering tPA prior to EVT did not improve the probability of successful reperfusion with EVT for an LVO patient (i.e. the probabilities of successful reperfusion with tPA and EVT for an LVO patient are independent), and that an LVO patient has a 74% chance of successful reperfusion given EVT. For the MS simulation, $v_p$ values were first apportioned from the distribution of $n_{LVO}$ into two groups—those that will reperfuse given EVT and those that will not. Each node's respective $t_{treatment|LVO,\ MS,\ EVT}$ and the proportion of $v_p$ values that will reperfuse from EVT were inputted into Equation 3 to yield time-evolved LVO infarct core volumes (i.e. final infarct core volumes). The remaining $v_p$ values maintained non-evolved LVO penumbra volume because it was assumed that a patient who does not reperfuse from any treatment will eventually have an infarct core that achieves the total ischemic penumbra volume $v_p$.

The probability of successful reperfusion with tPA for non-LVO patients was time-dependent. $v_p$ was apportioned from the distribution of $n_{non\text{-}LVO}$ into two groups—those that will reperfuse given tPA and those that will not. Each node's respective $t_{treatment|non\text{-}LVO,\ MS,\ tPA}$ and the proportion of $v_p$ values that will reperfuse from tPA were inputted into Equation 3 to yield time-evolved non-LVO infarct core volumes, and the remaining $v_p$ values maintained non-evolved non-LVO penumbra volume. The set of time-evolved non-LVO infarct core volumes and the set of non-evolved penumbra volumes were aggregated with the time-evolved and non-evolved LVO volumes computed previously. The combined set consisting of 75% non-LVO and 25% LVO volumes was mapped to 90-day mRS outcomes via Equation 6, yielding a cumulative distribution function of continuous 90-day mRS outcomes on the interval [0,6] for a general population of stroke patients that follow the MS transportation strategy for each of 7,690 nodes of interest in Travis County and each of 11,959 nodes of interest in Bastrop County.

For the DNS simulation, $v_p$ values were apportioned from the distribution of $n_{LVO}$ into three groups—those that will successfully reperfuse given tPA at the PSC (20%), those that will reperfuse given EVT at the CSC (74% of the remaining $n_{LVO}$), and those that will not reperfuse from either treatment. Each node's respective $t_{treatment|non\text{-}LVO,\ DNS,\ tPA}$ and the proportion of $v_p$ values that will reperfuse from tPA, as well as $t_{treatment|LVO,\ DNS,\ EVT}$ and the proportion of $v_p$ values that will reperfuse from EVT, were separately inputted into Equation 3 to yield two sets of respectively time-evolved LVO infarct core volumes. The remaining $v_p$ values in each pickup location where there was no reperfusion from either treatment maintained non-evolved LVO penumbra volume as in the MS simulation.

Non-LVO patients in the DNS simulation did not proceed past the PSC, as the provision of tPA is sufficient. Thus, the same stratifications of $n_{non\text{-}LVO}$ in the MS simulation were used, but now each node's respective $t_{treatment|non\text{-}LVO,\ DNS,\ tPA}$ was inputted into Equation 3 to yield a set of time-evolved non-LVO infarct core volumes. The set of time-evolved non-LVO infarct core volumes and the set of non-evolved non-LVO penumbra volumes were aggregated with the DNS time-evolved and non-evolved LVO volumes computed previously. The final set consisting of 75% non-LVO and 25% LVO volumes was mapped to 90-day mRS outcomes via Equation 6, yielding a cumulative distribution function of continuous 90-day mRS outcomes on [0,6] for a general population of stroke patients that follow the DNS transportation strategy for each of 7,690 nodes of interest in Travis County and each of 11,959 nodes of interest in Bastrop County.

Figure 8A:
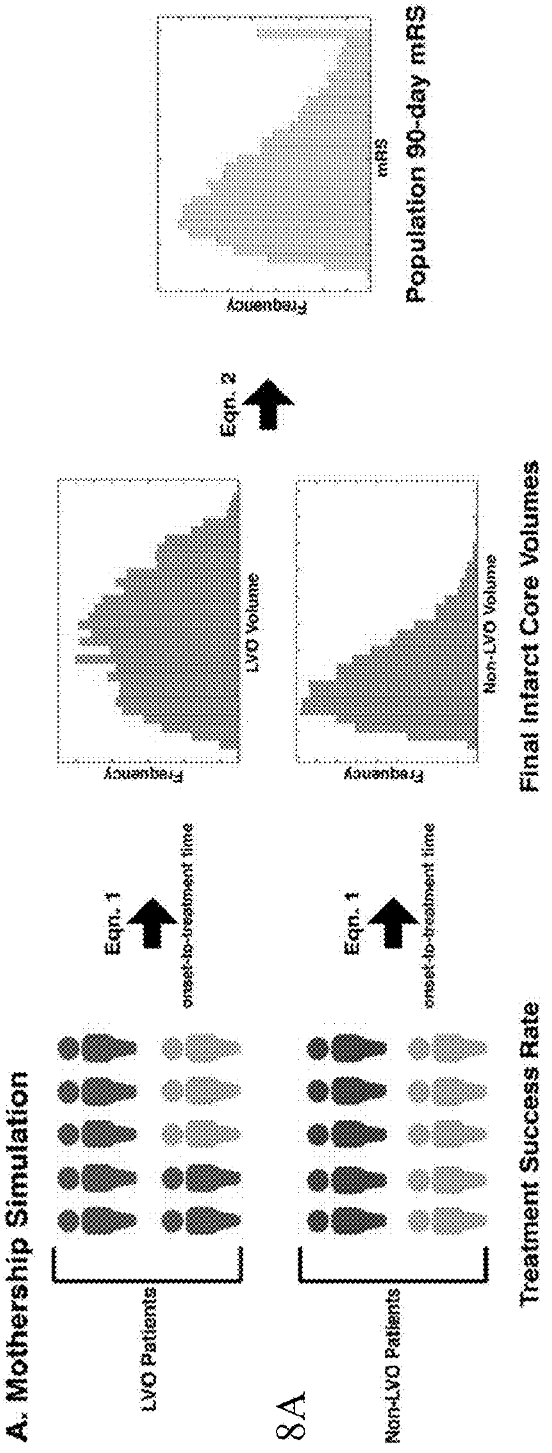
FIG. 8A and FIG. 8B depict exemplary emergency stroke transport simulations run in each node of interest.
Figure 8B:
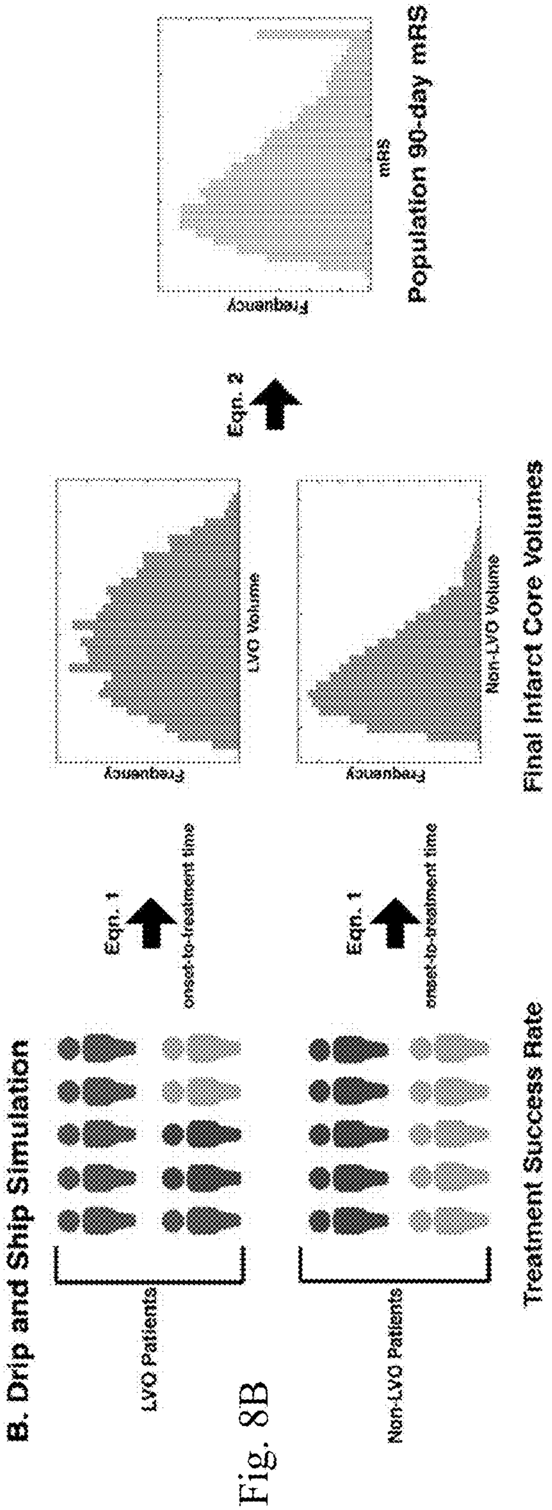

All probabilities of successful reperfusion were taken from clinical studies Table 2, as shown below, presents framework reperfusion parameters. FIG. 8A and FIG. 8B visualize the simulation framework. Furthermore, a 4.5-hour onset-to-treatment time window was taken as the acceptable window for tPA administration. All non-LVO patients that took longer than 4.5 hours to receive tPA mapped their non-evolved $v_p$ directly to 90-day mRS, and LVO patients on the DNS track that arrived at the PSC after the time window were not considered for tPA treatment.

TABLE 2

Percentage of the 13,000 simulated patients in each node that successfully reperfuse or do not reperfuse based on stroke type, transport strategy and treatment type. An LVO patient has a 74% chance of successful reperfusion with EVT,[26] and a 20% chance of successful reperfusion with tPA.[27]

| | |
|---|---|
| **LVO (n = 3900 patients), Mothership** | |
| Reperfuses with tPA | 0% |
| Reperfuses with EVT | 74.0% |
| Does not reperfuse | 26.0% |
| **LVO (n = 3900 patients), Drip and Ship** | |
| Reperfuses with tPA | 20.0% |
| Reperfuses with EVT | 59.2% |
| Does not reperfuse | 20.8% |
| **Non-LVO (n = 9100), Mothership or Drip and Ship** | |
| Reperfuses with tPA | ‡ |
| Does not reperfuse | ‡ |

‡ The probability of successful reperfusion with tPA for non-LVO patients is time-dependent.

Framework Assumptions

As with any model, a few assumptions were made in order to focus the scope of the study. First, all patients in the simulated population had a prehospital mRS of 0, as future studies are necessary to better understand stroke growth mechanisms in nonzero pre-hospital mRS subgroups. Secondly, all non-LVO and LVO patients were eligible for tPA and all LVO patients were eligible for EVT. The inclusion of those who do not meet treatment eligibility criteria would likely create negligible and inconsequential differences in the cumulative distribution functions of 90-day mRS and therefore simulation results. Thirdly, the present population of stroke patients did not include stroke mimic cases, or intracerebral hemorrhage cases. An extensive review of the literature by a previously published simulation study concluded that mimic and hemorrhage cases can be considered to have a time invariant probability of a good outcome. Clinical trials show that interventions of hemorrhagic stroke in the hyperacute window post-onset do not improve outcomes relative to standard of care. Because bypass times in the Travis and Bastrop Counties are <1 hour, including this subgroup would not affect simulation results.

From a clinical perspective, it was assumed that for patients who respond to treatment, successful reperfusion occurred with negligible delay and infarct core growth was halted. It is possible that treatment-to-reperfusion time intervals are not negligible, and if so, the disclosed framework results likely underestimate MS favorability. Additionally, the probabilities of successful reperfusion given EVT or tPA for LVO patients were independent of time from onset of acute ischemic stroke. If these probabilities decrease with time in actuality, then the present simulation results likely underestimate DNS favorability. While Menon et al show that the probability of successful reperfusion for LVO patients has a dependency on time from treatment with tPA, their model does not discuss the likely dependence of these results on patient-specific onset-to-treatment times. In order to integrate their model with the present framework, data that relates the stroke onset-to-treatment and treatment-to-reperfusion windows is necessary.

Finally, it was assumed that the transport decision made by EMS at the pickup location was carried through completely and there was no switch to another method of transportation at any point thereafter.

Case Study 1: Optimal Transport Decisions Analysis

Figure 9:
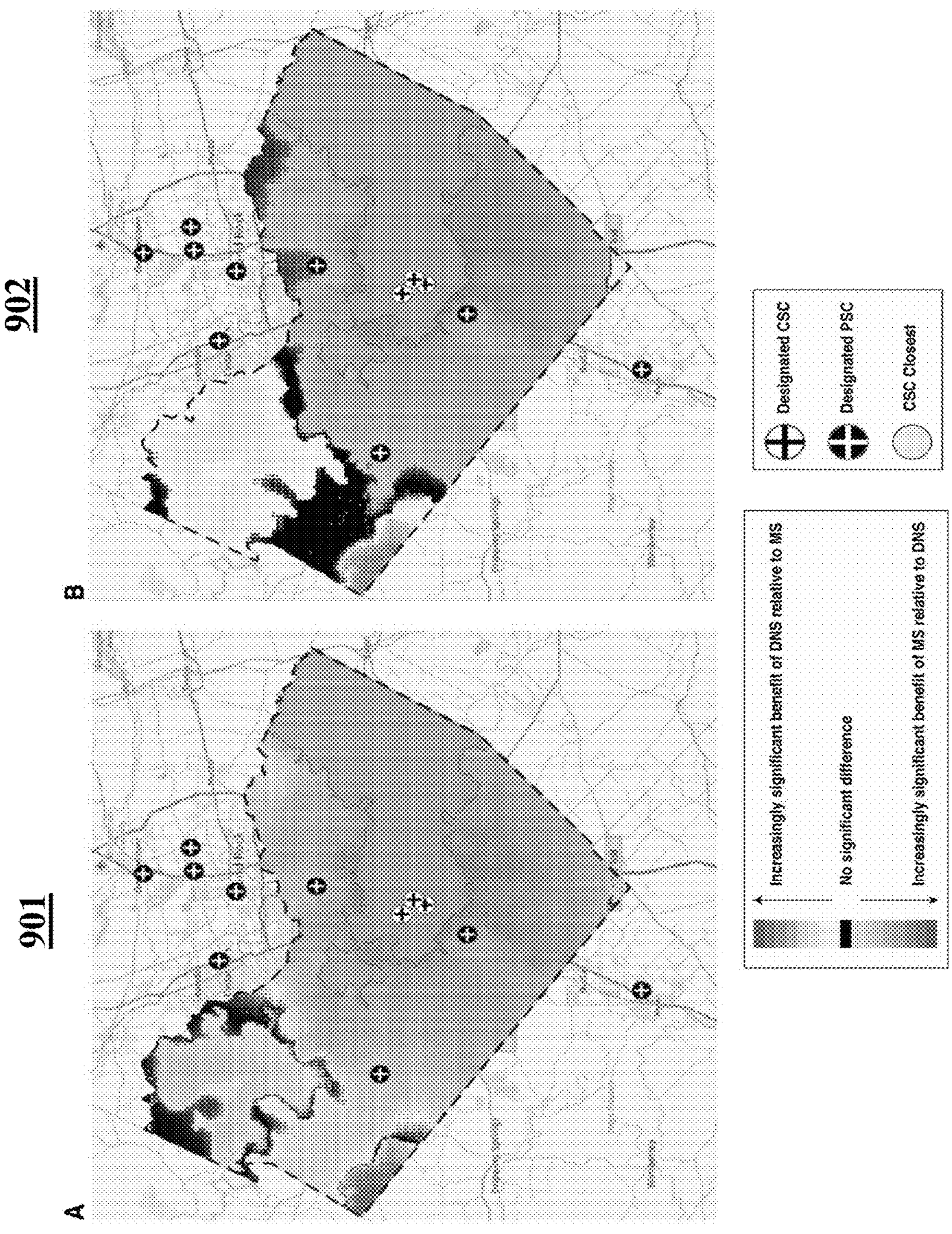
FIG. 9 depicts a heatmap showing Cohen's d effect size. Assuming a fast rate of non-LVO infarct core growth, DNS yields more relative benefit in the northwest region bounded by the Colorado River compared to when a slow rate of non-LVO infarct core growth is assumed. With either choice of non-LVO infarct core growth rate, the magnitude of MS statistical significance decreases as the transport time to the CSCs in the city-center increases (relative to the transport time to the nearest PSC).

In order to determine which transport strategy provides significantly better probabilities of a good outcome (90-day mRS 0-2) for each node of interest in a given county, the probability of a good outcome was extracted respective to DNS and MS from their cumulative distribution functions outputted by the emergency stroke transport simulations. These simulations and extractions were repeated twenty times, yielding a distribution of twenty distinct probabilities of a good outcome given DNS and twenty distinct probabilities of a good outcome given MS for every node of interest. A 2-sample, one-sided Kolmogorov-Smirnov test compared the shape of these two distributions within each node and determined which transport strategy provides significantly better probabilities of a good outcome (a=0.01 level). In addition to the Kolmogorov-Smirnov test, a 2-sample student t-test was performed to determine statistical significance between the means of the DNS and MS distributions of a probability of a good outcome in each node (a=0.01 level). These two statistical tests provided a useful combination that can detect, respectively, significant differences between the variances and means of the distributions in question. Furthermore, the Cohen's d statistic was used for effect size to quantify the magnitude of statistical significance in the nodes that favor DNS or MS. Cohen's d is a metric of practical significance that measures the standardized difference in means (extent of overlap or separation between distributions), in units of standard deviations, between the DNS and MS distributions of 90-day mRS good outcomes. QGIS mapping software (QGIS Development Team, v3.12) was used for visualizing statistical results. FIG. 9 presents the Cohen's d results for Travis County using the empirically calculated standard deviations for the probability of a good outcome measured across each node's Monte Carlo simulations.

Figure 10:
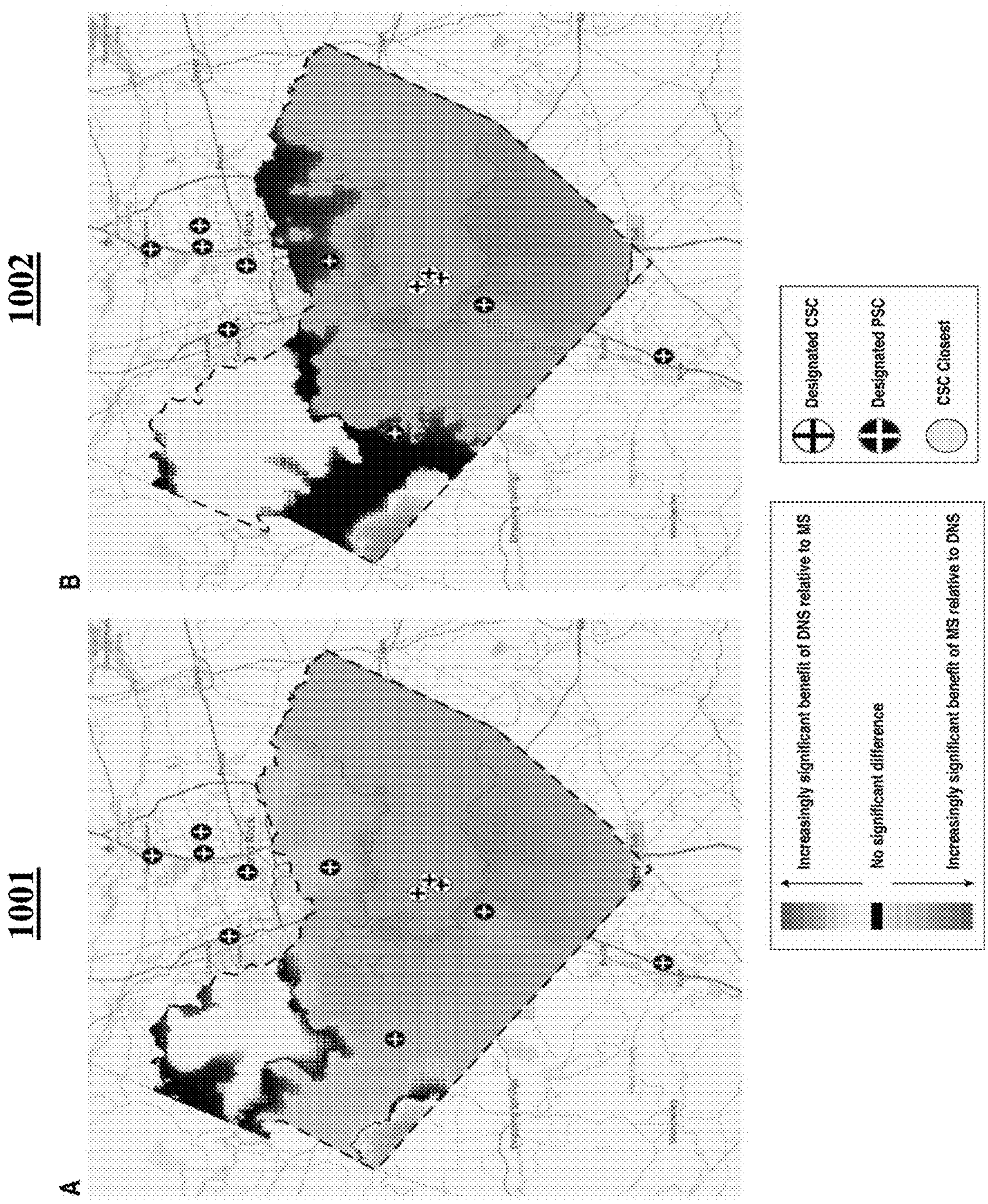
FIG. 10 depicts the heatmap of FIG. 9 re-colored by the adapted, single-individual-based Cohen's d effect size for Travis County. Map 1001 assumes a fast rate of non-LVO infarct core growth, and map 1002 assumes a slow rate. This colormap has subtle differences from FIG. 9 (mostly due to the inherent stochasticity of the simulations), but the relative magnitudes of effect size amongst each set of measurements are largely equivalent. As such, the figures yield similar interpretations—the MS transport strategy's effective significance dissipates as the patient pickup locations become increasingly far from the CSCs.

An alternative Cohen's d effect size calculation was also considered in terms of the variance of a Bernoulli distributed random variable with the specified value of the probability of a good outcome when computing the pooled standard deviation. This alternative variance calculation considers the respective means of the DNS and MS distributions of a probability of a good outcome in each node. As a result, this adapted effect size metric can be interpreted as the effect on a single individual who is transported with a particular strategy given the two probabilities, whereas using the pooled standard deviation on the probability of a good outcome from the simulations calculates an effect size that can be interpreted as the collective effect on many individuals. FIG. 10 presents the results of the simulation with consideration to this adapted Cohen's d metric. It was found that the coloring of FIG. 9 and FIG. 10 is largely equivalent because the relative magnitudes of effect size amongst the non-adapted and adapted Cohen's d measurements are the same, though the quantities themselves differ in scale. Variations in the number of nodes that favor a certain transport strategy or that are non-significant between FIG. 9 and FIG. 10 is attributable to modeling stochasticity that results from running independent simulations (i.e. volume distributions are re-generated between independent runs, creating slight differences in simulation results).

Case Study II: Optimal Bypass Policy Analysis

Bypass time is defined as the added transport time taken to reach the more distant CSC from the pickup location compared to going directly to the closer PSC. There are bypass policy recommendations provided by the American Heart Association and by regional health care networks establishing that if the bypass time from a given pickup location exceeds the policy recommended threshold, then a patient suspected to have an LVO should be transported directly to the PSC.

The Tiger/Line Shapefiles published online annually by the United States Census Bureau provide population data for the 580 geographic census block-groups in Travis County (2010 census total county population ~1.03 million). Each block-group's population was uniformly distributed amongst the nodes in its geographic boundaries. For example, if a census block-group with a population of 1000 enclosed 100 nodes, then each node in that block-group would be assigned a population of 10. Using this census data and the node-specific probabilities of a good outcome outputted by the simulation, the number of people with a good outcome per 1000 stroke cases in Travis County was assessed under a range of bypass policies, without LVO field testing. These results were compared to an ideal threshold of stroke care, defined as the number of people with a good outcome per 1000 stroke cases if EMS utilized an LVO field test with 100% sensitivity and specificity, and always transported the patient to the center that provides the highest probability of a good outcome for their stroke type. The bypass policy that yields the smallest deviation in the number of people with a good outcome per 1000 stroke cases from the ideal threshold is considered the optimal county-wide bypass policy without LVO field testing.

This methodology was also extended to incorporate common LVO field tests, such as the Los Angeles Motor Scale (LAMS≥4; sensitivity=0.66, specificity=0.86), Cincinnati Prehospital Stroke Severity Scale (CPSSS≥2; sensitivity=0.56, specificity=0.86), and the Prehospital Acute Stroke Severity scale (PASS≥2; sensitivity=0.71, specificity=0.84). For each field test, a range of bypass policies was employed for suspected LVO patients only, while always sending those with a negative test to the PSC. Assessing the number of people with a good outcome per 1000 stroke cases in Travis County, the same ideal threshold as before was used to determine the optimal county-wide bypass policy. These analyses were repeated for Bastrop County (39 block-groups, 2010 census total county population ~74.17 thousand).

Results

Optimal Transport Decisions

Of the 7,690 nodes of interest in Travis County, it was found that DNS provides significantly better probabilities of a good outcome in 13.3% and MS provides significantly better probabilities of a good outcome in 74.2%, assuming a fast rate of non-LVO infarct core growth (KS-test, student t-test: $P<0.01$; graph 1101 in FIG. 11). The remaining 12.5% are not statistically significant in either direction.

Assuming a slow rate of non-LVO infarct core growth, DNS provides significantly better probabilities of a good outcome in 24.0% of the nodes of interest and MS provides significantly better probabilities of a good outcome in 59.8% (KS-test, student t-test: $P<0.01$; graph 1102 in FIG. 11). The remaining 16.2% are not statistically significant in either direction.

Of the 11,959 nodes of interest in Bastrop County, it was found that DNS never provides significantly better probabilities of a good outcome and MS provides significantly better probabilities of a good outcome in 57.6%, assuming a fast rate of non-LVO infarct core growth (KS-test, student t-test: $P<0.01$). The remaining 42.4% are not statistically significant in either direction.

Figure 12:
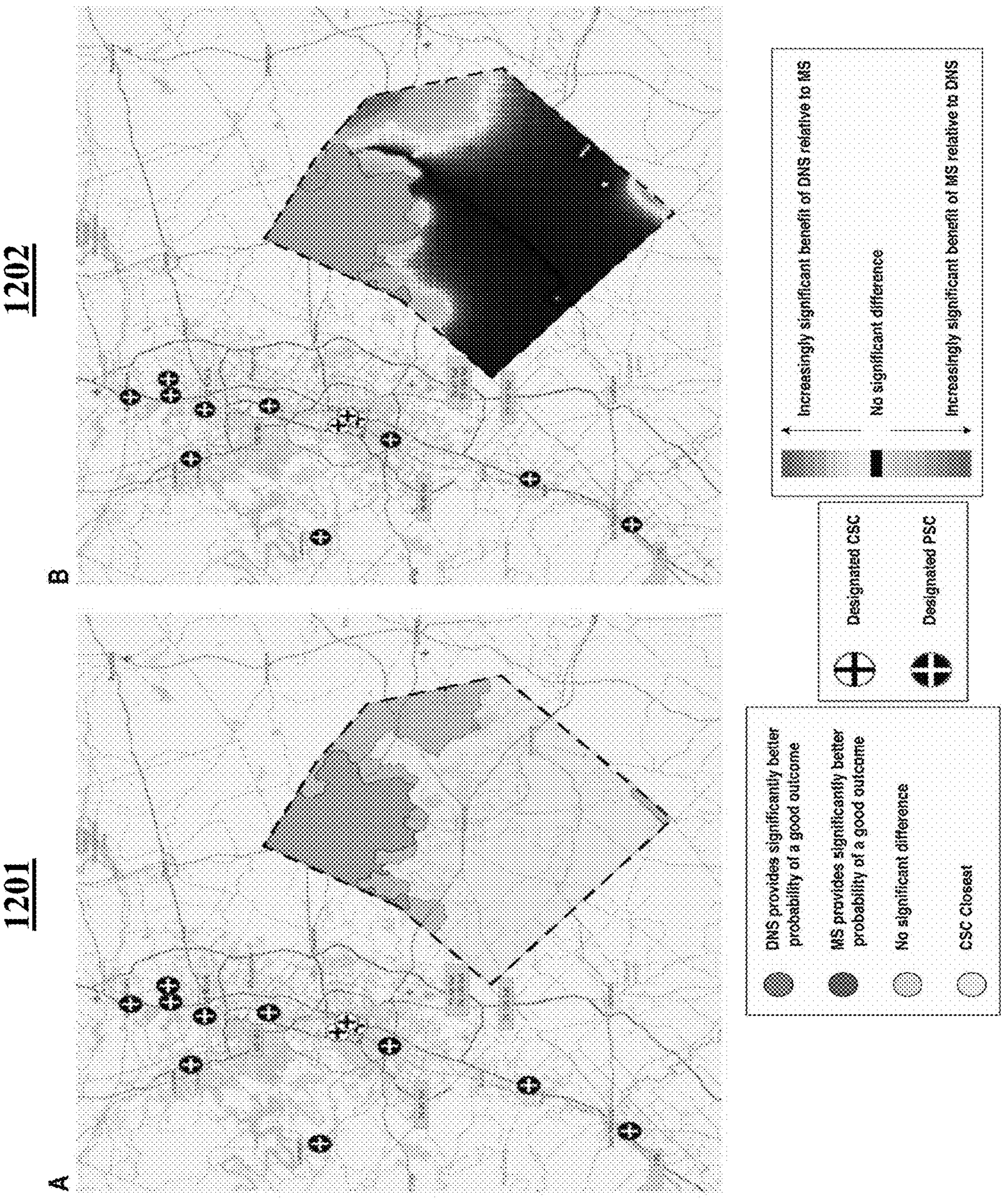
FIG. 12 depicts exemplary results demonstrating that, in Bastrop County, under the assumption of a slow rate of non-LVO infarct core growth, the DNS transport strategy provides significantly better probabilities of a good outcome in more nodes of interest than MS (map 1201). However, a majority of the region does not statistically favor either transport strategy. Map 1202 is the corresponding effect size plot colored by the non-adapted Cohen's d.

Assuming a slow rate of non-LVO infarct core growth, DNS provides significantly better probabilities of a good outcome in 11.3% of the nodes of interest and MS provides significantly better probabilities of a good outcome in 7.1% (KS-test, student t-test: $P<0.01$; graph 1201 in FIG. 12). Graph 1202 is the heatmap of Bastrop County colored by non-adapted Cohen's d effect size statistic under the assumption of a slow rate of non-LVO infarct core growth. The remaining 81.6% are not statistically significant in either direction.

FIG. 9 presents heatmaps of Travis County colored by Cohen's d effect size statistic, showing dissipation of the effective significance of the MS transport strategy over DNS when considering pickup locations that are increasingly distant from CSCs.

The northwest corner of Travis County is one of the most isolated locations from road and highway access in Travis County because the Colorado River encompasses it (the river is most easily discernible on FIG. 5). It can be seen that the regions of insignificance in this corner under the assumption of a fast rate of non-LVO infarct core growth (graph 1101 in FIG. 11 or graph 901 in FIG. 9) convert to DNS significant when assuming a slow rate instead (graph 1102 or graph 902).

Optimal Bypass Policies

Figure 13:
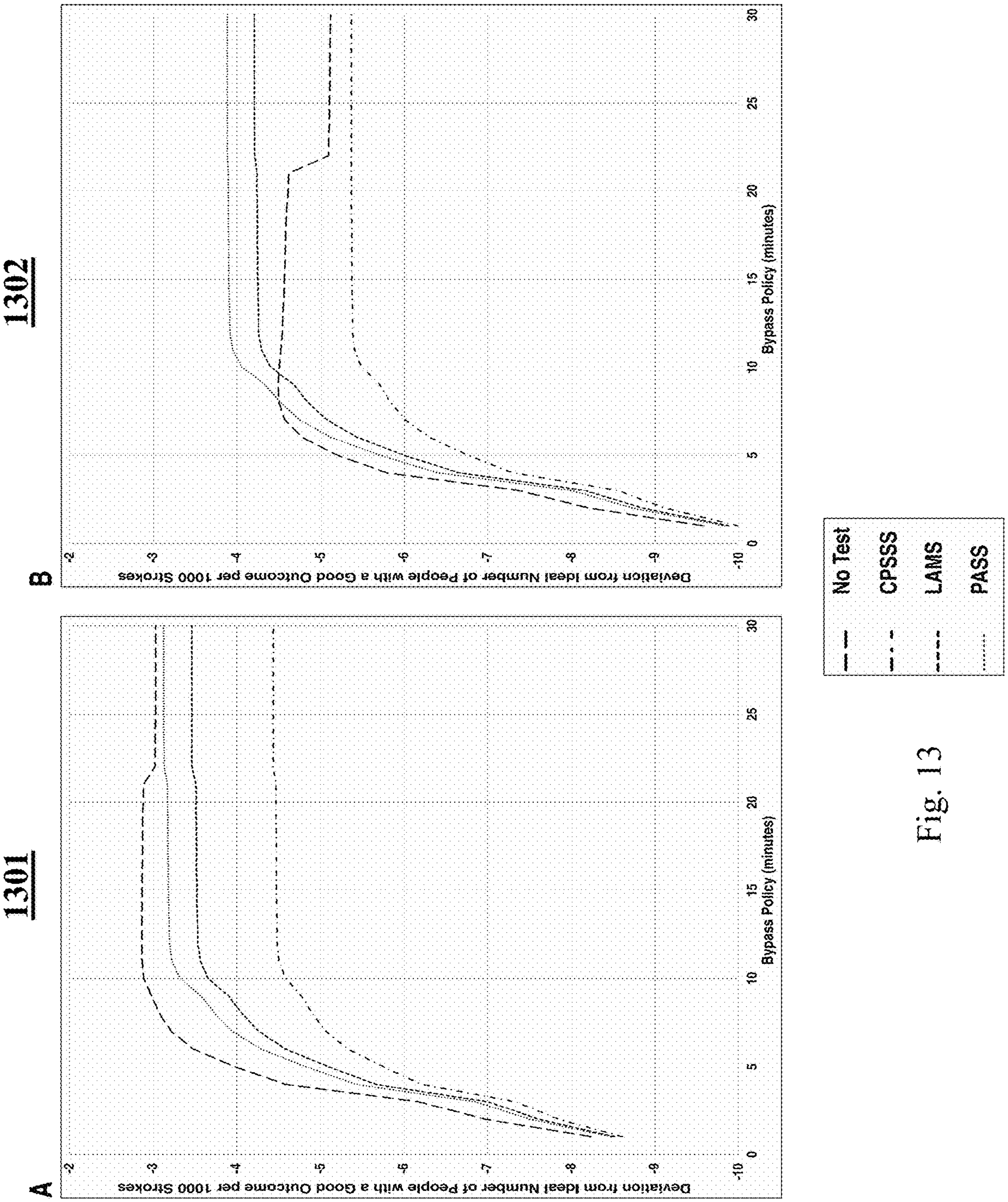
FIG. 13 depicts exemplary results showing that, assuming a fast rate of non-LVO infarct core growth, bypass policies 10- through 21-minutes are optimal without LVO field testing (graph 1301). Under the assumption of a slow rate of non-LVO infarct core growth, employing the LAMS or PASS field tests and always sending suspected LVO patients directly to the CSC is optimal (graph 1302).

With reference to FIG. 13, in Travis County, bypass policies from 10- through 21-minutes without LVO field testing yield the optimal number of people with a good outcome per 1000 strokes, assuming a fast rate of non-LVO infarct core growth (graph 13A). Furthermore, graph 13A shows that implementing any LVO field test in conjunction with bypass policies only for suspected LVO patients decreases the number of people with a good outcome per 1000 strokes.

Under the assumption of a slow rate of non-LVO infarct core growth, administering LAMS or PASS and always sending suspected LVO patients directly to the CSC is optimal (graph 13B). However, utilizing the CPSSS LVO field test with bypass policies only for suspected LVO patients yields fewer people with a good outcome per 1000 strokes than implementing bypass policies without LVO field testing.

The Bastrop County statistical significance analysis yields a great deal of variation in transport strategy favorability depending on the rate of non-LVO infarct core growth, and its optimal bypass policies are similar to Travis County.

Figure 14:
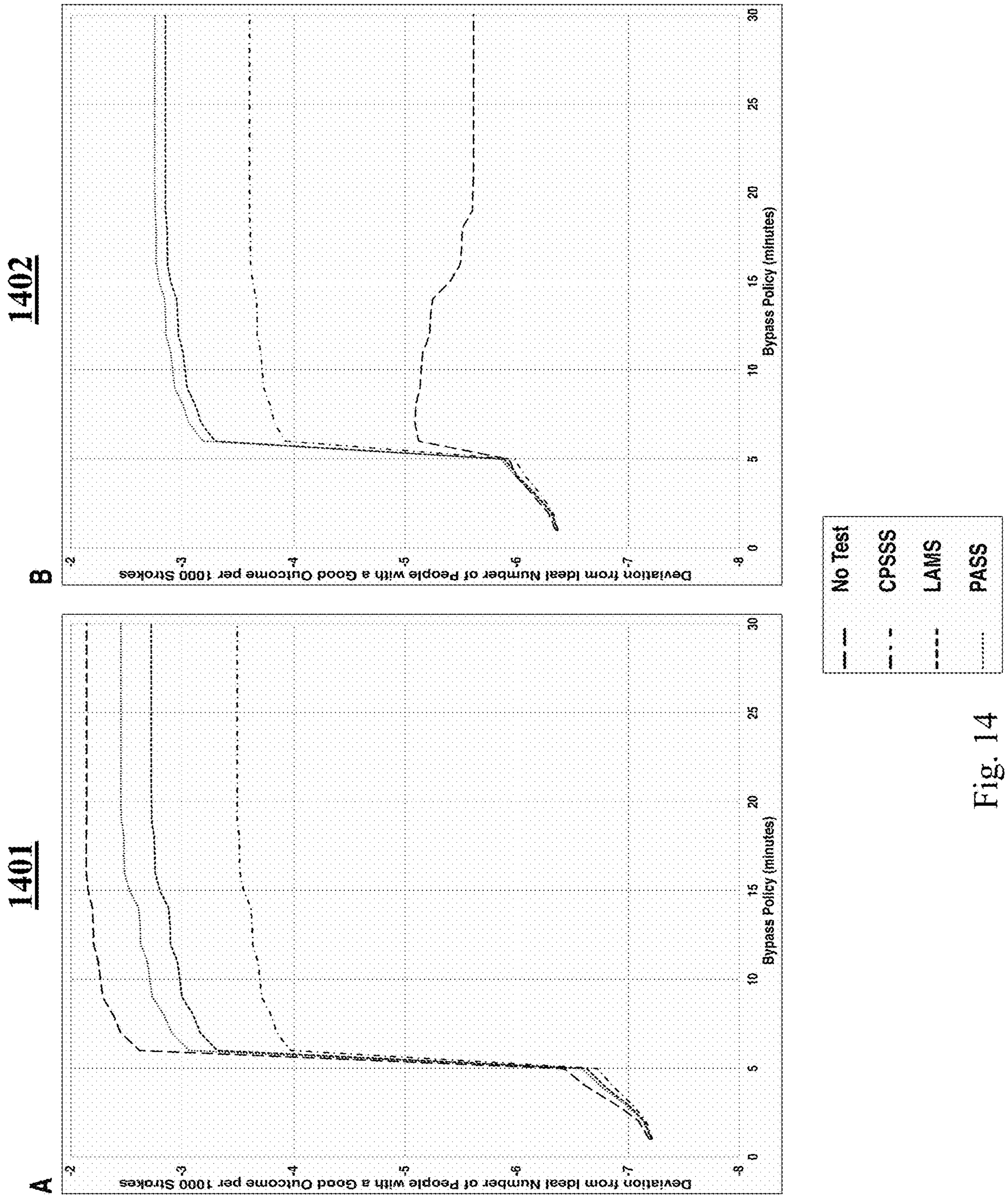
FIG. 14 depicts exemplary results demonstrating the efficacy of Bastrop County bypass policies relative to the ideal threshold. Under the assumption of a fast rate of non-LVO infarct core growth (graph 1401), always going directly to the more distant CSC is optimal without LVO field testing. If a slow rate is assumed (graph 1402), then implementing any of the three field tests and always sending suspected LVO patients to the CSC is optimal.

With reference to FIG. 14, in Bastrop County, always bypassing the PSC without field testing yields the optimal number of people with a good outcome per 1000 strokes, assuming a fast rate of non-LVO infarct core growth (graph 1401). Furthermore, graph 1401 shows that implementing any LVO field test in conjunction with bypass policies only for suspected LVO patients decreases the number of people with a good outcome per 1000 strokes.

Conversely, under the assumption of a slow rate of non-LVO infarct core growth, administering any field test and always sending suspected LVO patients to the CSC is optimal and yields a greater number of people with a good outcome per 1000 strokes than if bypass policies were implemented without LVO field testing (graph 1402).

Sensitivity Analysis

Figure 15A:
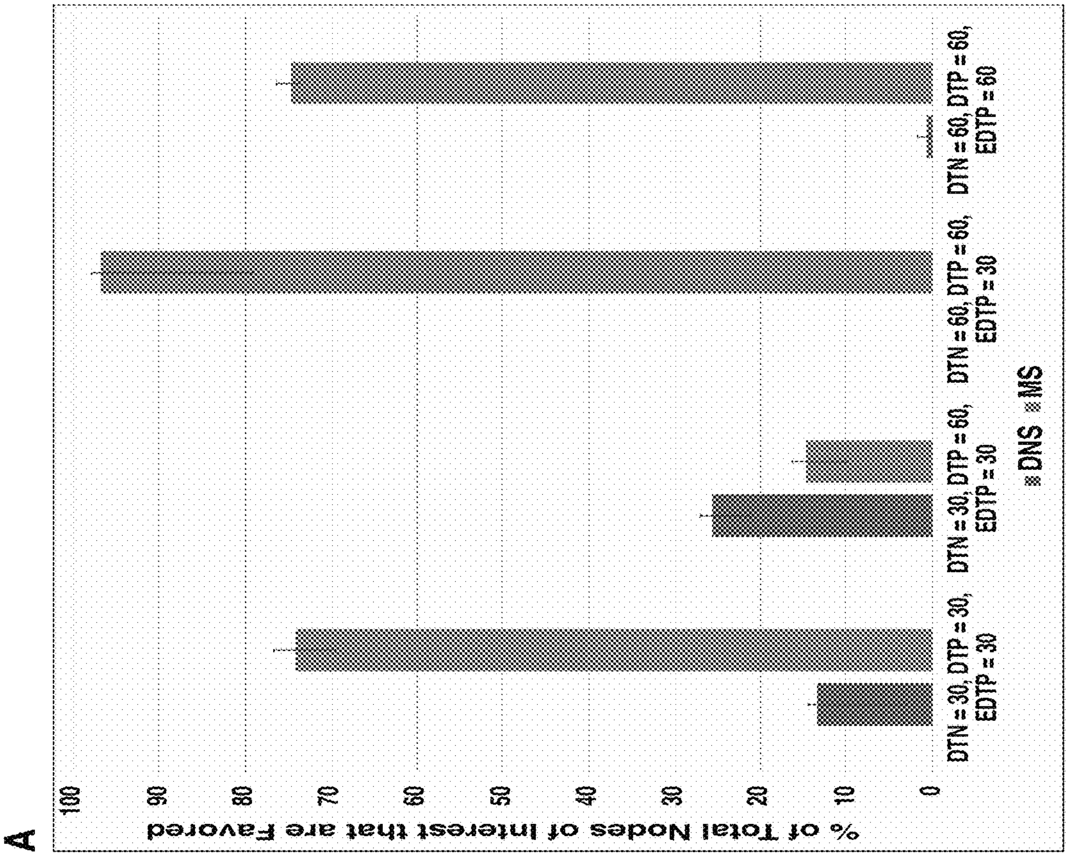
FIG. 15A and FIG. 15B depict exemplary results demonstrating the sensitivity analysis of hospital time interval parameters in Travis County, under the assumption of a fast (FIG. 15A) or slow (FIG. 15B) rate of non-LVO infarct core growth. The error bars reflect variation in simulation results due to the uncertainty in the outcome-volume relationship (Equation 6, as shown in the Experimental Examples below).
Figure 15B:
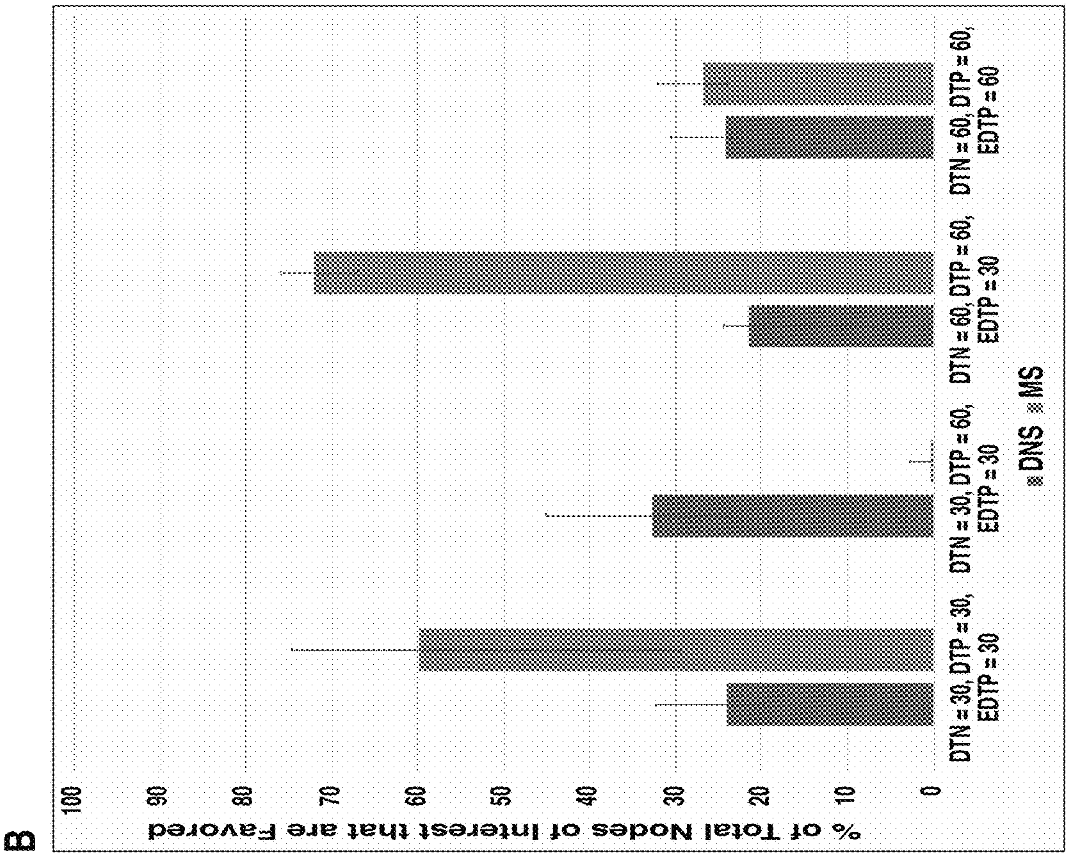

FIG. 15A and FIG. 15B visualize the percentage of the total nodes of interest that significantly favor a given transport strategy in Travis County (KS-test, student t-test: $P<0.01$) under four different combinations of door-to-needle (DTN), door-to-puncture (DTP), and expedited-door-to-puncture (EDTP; for LVO's identified at the PSC that are then transported to the CSC) time interval model parameters, including the combination of parameters considered in the main text (DTN=30 minutes, DTP=30 minutes, EDTP=30 minutes). Assuming a fast rate of non-LVO infarct core growth, MS is significantly favored by a greater percentage of nodes than DNS in each of the scenarios considered except when the DTP time at the CSC is greater than the DTN at the PSC (FIG. 15A).

Figure 16B:
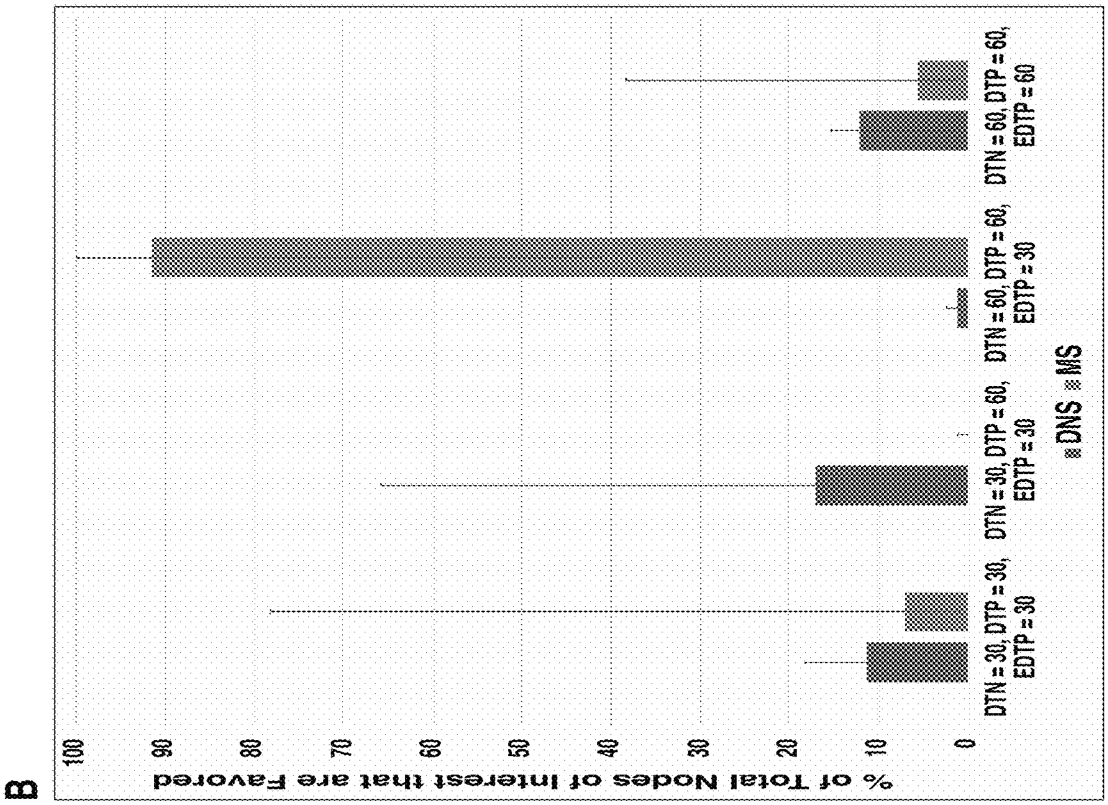
FIG. 16A and FIG. 16B depict exemplary results demonstrating the sensitivity analysis of non-transport time interval parameters in Bastrop County, under the assumption of a fast (FIG. 16A) or slow (FIG. 16B) rate of non-LVO infarct core growth. The error bars reflect variation in simulation results due to the uncertainty in the outcome-volume relationship (Equation 6, as shown in the Experimental Examples below).
Figure 16A:
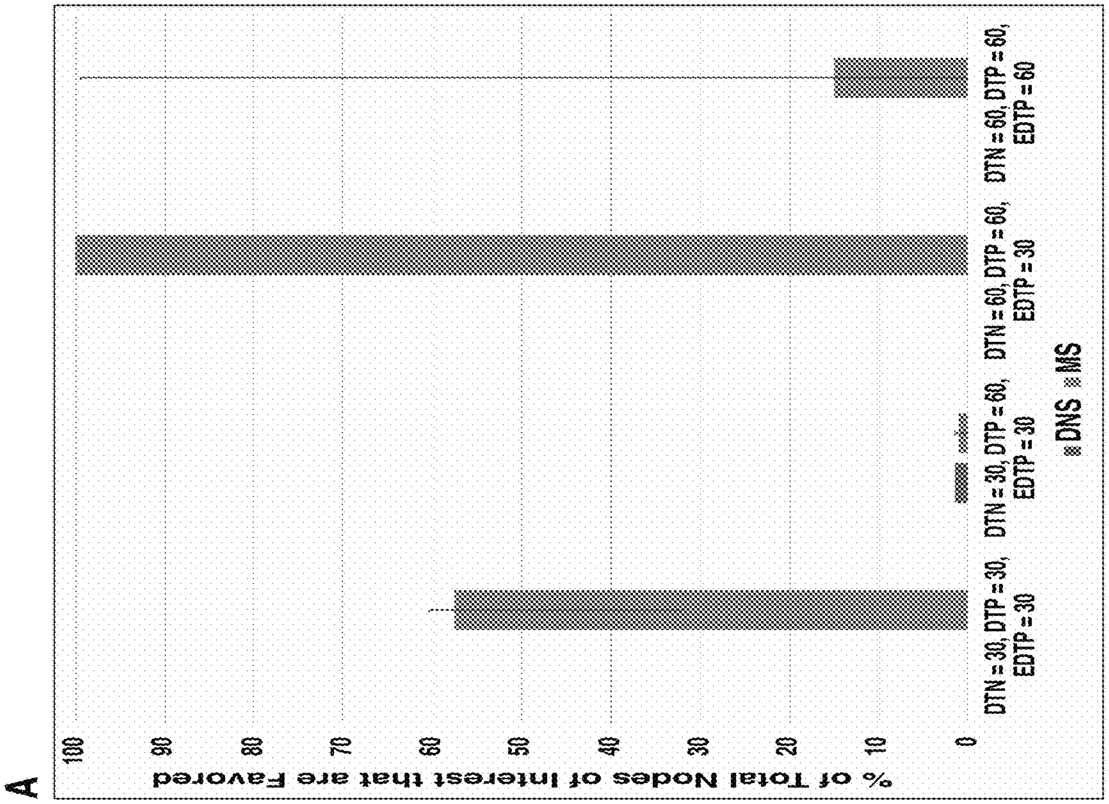

FIGS. 16A and 16B present the same sensitivity analysis for Bastrop County, with FIG. 16A showing that DNS is essentially never favored by any nodes of interest in the county, under the assumption of a fast rate of non-LVO infarct core growth.

The error bars in both sensitivity analyses represent the variation in results due to uncertainty in the outcome-volume relationship. Though the uncertainty in the relationship itself is small, it amplifies the uncertainty in the simulation study results. This phenomenon can be explained by the sensitivity of the statistical significance tests to 'boundary cases,' which are the nodes of interest that significantly favor a transport strategy given small changes in model parameters but that do not actually favor the transport strategy in any practical sense (small effect size). It was observed that the Bastrop County results are quite variable compared to Travis County because nodes in Bastrop County tend to be further from any stroke center, leading to nodes that are highly sensitive to slight adjustments in model parameters. In future studies, it would be useful to determine the most clinically relevant effect size cutoff in order to eliminate these negligible, practically insignificant nodes and consequentially reduce the variation between and within (error bars) each scenario.

Discussion

Herein, a framework has been proposed with a physiology-based, mathematical model of infarct core growth. Monte Carlo methods allow one to generate synthetic patient data, and emergency stroke transport simulations outputted distributions of 90-day mRS outcomes corresponding to DNS and MS in every node. Although the probability of a good outcome was deemed the most clinically relevant metric, this framework has the capability to also make statistical comparisons between the transport strategies with respect to all outcomes 0-6 on the 90-day mRS scale. An analysis of the comprehensive outcome scale would be particularly useful in studying burdens of cost or other healthcare value metrics, such as cost-effectiveness models that seek to optimally place new stroke centers or upgrade existing centers by equilibrating healthcare costs and patient outcomes.

This work builds on previous, foundational studies of emergency stroke transportation. Some of these studies compare the two emergency stroke transport strategies using conditional probability models derived from large clinical datasets, and are able to compute probabilities of a good outcome on the 90-day mRS scale, dependent on the time from stroke onset to treatment, the type of stroke and corresponding treatment, and the particular transport strategy. This data-driven approach of emergency stroke transportation modeling offers validity and accuracy only within the bounds of the dataset (i.e. the patients and geographic times the model is derived from), and cannot identify underlying patient-specific, physiological mechanisms that account for trends in the data. The proposed framework serves as a foundation to resolve these issues by providing a ground-up model that accounts for inherent, population-level variability, or stochasticity, of physiology-based independent variables. As a result, the framework can be applied to any geography, and cause-effect relationships motivating the results of the study are easily identifiable. Furthermore, it can determine statistically significant differences in outcomes between emergency stroke transportation strategies contingent on the stochasticity of these clinically relevant independent variables, whereas the data-driven models are deterministic in their current form and do not compute statistical significance.

In the first case study, optimizing transport decisions, it was shown that in both counties a fast rate of non-LVO infarct core growth decreases the number of nodes that favor DNS and increases the number of nodes that favor MS compared to when a slow rate is assumed. From a physiological perspective, if a non-LVO patient's infarct core growth rate is fast and their pickup location is sufficiently remote from any stroke center, then their infarct core will quickly achieve a significant proportion of the ischemic penumbra volume before time of treatment, regardless of transport strategy. By extension, the non-LVO subpopulation's distribution of final infarct core volumes will differ marginally between strategies, so DNS will not provide significantly better good outcomes as often for a mixed stroke population transported from these locations. This case study also reveals that geographies with long onset-to-treatment times (e.g. Bastrop County) are likely to have a greater proportion of nodes that do not significantly favor any strategy relative to geographies closer to stroke centers (e.g. Travis County), irrespective of infarct core growth rates. As onset-to-treatment time increases, the likelihood that any stroke patient's infarct core will achieve a significant proportion of the penumbra volume before treatment also increases. When transport times are exceptionally long, final infarct core volumes are approximately equal, translating to a lack of statistical favorability towards either transport strategy.

The physiological rationale for cases in which there is no statistical significance between DNS and MS may lend some insight into the recent, preliminary results of the RACECAT study. In particular, they report that there was no benefit in outcomes due to the choice of emergency stroke transport in Catalonia, Spain. Catalonia's mean transport times to the nearest PSC and nearest CSC exceed the rural Bastrop County's by approximately 42 minutes and 110 minutes respectively. Although more information is needed, it is postulated that Catalonia's exceptionally long transport times led to considerable growth of patient infarct core volumes with either transport strategy. Consequently, there were negligible differences between the distributions of final infarct core volumes, and therefore outcomes, corresponding to patients randomly assigned to DNS or MS.

Figure 11:
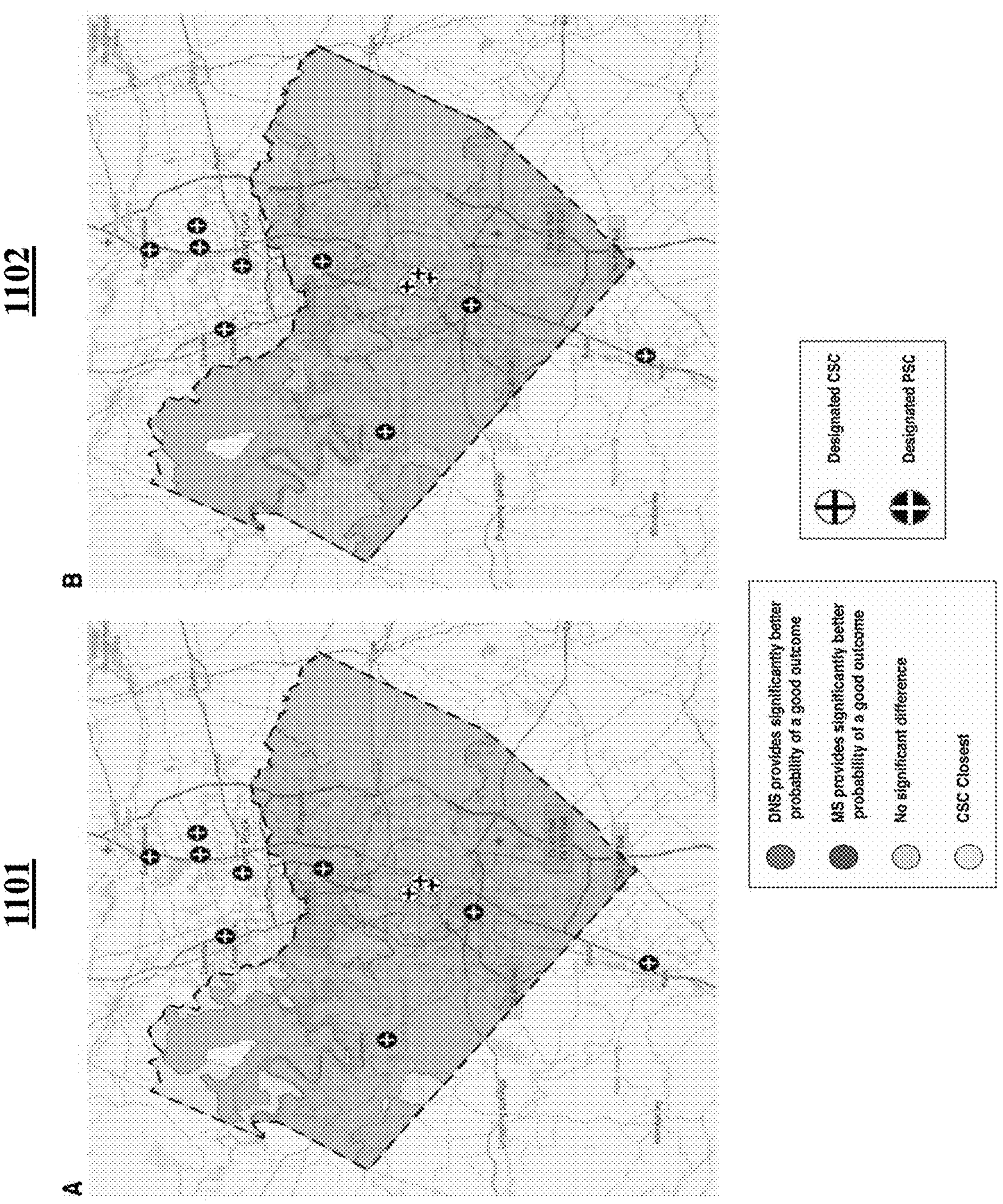
FIG. 11 depicts exemplary results demonstrating that DNS provides a significantly better probability of a good outcome (90-day mRS 0-2) in fewer nodes assuming a fast rate of non-LVO infarct core growth (map 1101) compared to when slow rate is assumed (map 1102). MS provides significantly better probabilities of a good outcome in fewer nodes if the non-LVO infarct core growth rate is slow (map 1102) compared to when a fast rate is assumed (map 1101). Access to transportation routes can account for the difference between DNS and MS favorability, as seen in the northwest region of Travis County. Note that the colorless area in the northwest region is occupied by the Balcones Canyonlands National Wildlife Refuge and does not contain any nodes.

In addition, the analysis of optimal bypass policies in the second case study revealed counterintuitive results. It was found that under the assumption of a fast rate of non-LVO infarct core growth in either county, implementing any LVO field test in conjunction with bypass policies only for suspected LVO patients performs worse than implementing bypass policies without LVO field testing. This result follows from the first case study, showing that under the same rate assumption, MS provides significantly better probabilities of a good outcome than DNS in a majority of Travis County (FIG. 11). These MS-favored regions cover the densely populated areas of Travis County (e.g. Austin proper and its suburbs), so a county-wide bypass policy completely washes out the DNS preference of the few, less-populated regions. By implementing LVO field tests, rates of misclassification inherent to these tests were introduced. Evidently, a majority of the county significantly favors MS, so misclassifying LVO patients as non-LVO and transporting them to the PSC causes substantial harm (false-negatives). The implementation of a bypass policy without LVO field testing eliminates this harm by transporting all patients directly to the CSC. Importantly, the outcomes of non-LVO patients transported from remote pickup locations do not differ significantly between DNS or MS under this rate assumption. Field testing therefore negligibly benefits the non-LVO subpopulation, and does not offset the harm done to the misclassified LVO patients taken to the PSC.

Conversely, assuming a slow rate of non-LVO infarct core growth, it was found that implementing LVO field tests in conjunction with bypass policies only for suspected LVO patients performed better than implementing bypass policies without LVO field testing (with the exception of CPSSS in Travis County). Under this rate assumption, the non-LVO's in remote pickup locations benefit significantly more from transport to the PSC. As a result, implementing bypass policies without LVO field testing harms the entire non-LVO subpopulation (false-positives and true-negatives alike), whereas field testing mitigates this harm by accurately classifying a proportion of the non-LVO patients for optimal transport to the PSC (true-negatives). The drastic differences in optimal emergency stroke transport policy stemming from the rate of non-LVO infarct core growth underscores the critical importance of gaining empiric data of the physiological kinetics of this stroke type's growth rate.

The present goal was to bring a new perspective to the discussion of emergency stroke transport by elucidating the relevance of physiology in decision-making. As noted previously, data-driven models map time from stroke onset to reperfusion directly to a probability of a good outcome. The present model generalizes this relationship by explicitly considering the underlying patient-specific, physiological variables that are fundamental determinants of stroke outcomes. By doing so, one is able to expand these clinically relevant factors to account for variation in a patient population, thereby gaining insight into the physiology that substantially influences optimal decisions.

While not being bound by scientific theory, it is believed that one could modify the Equation 3 time constant to accommodate age, hypertension, or other patient comorbidities that may also affect infarct core growth rates. Early knowledge of a patient's stroke type and degree of collateral blood flow with CT-capable ambulances would allow for personalized emergency transport decisions with the present framework. In addition, the time from stroke onset to reperfusion can be expanded into a statistical distribution to account for the inherent stochasticity of pre-hospital, transport and hospital time intervals found in a given geography and stroke center network (e.g. traffic, triage delays, etc.). These model capabilities pose valuable opportunities to tailor estimates with region-specific data that encapsulates as much realistically-occurring variability as possible.

As the mathematical understanding of stroke physiology improves, the present framework can provide more reliable estimates to inform transport decisions and policies. The present case studies highlight the importance for clinical studies that empirically measure infarct core growth rates in humans. The non-LVO infarct core growth rate is not currently defined by clinical data, but evidently has a large influence on optimal decisions and policies. In the same regard, the parameterization of the LVO time constant utilizes data from non-human experiments, which may affect the accuracy of the disclosed estimates. Moreover, while it remains to be seen if the 90-day mRS-volume relationship (Equation 6) varies by population, Ernst et al reports uncertainty in this association which directly translates to uncertainty in the disclosed modeling results (see Sensitivity Analysis above). The precision of the present estimates may improve with data that reports a 90-day mRS-volume relationship to a greater degree of confidence. Additionally, all probabilities of successful reperfusion are taken from clinical trials that define successful reperfusion as a Thrombolysis in Cerebral Infarction score >=2b, but scores >=2a will be considered in future work given clinical studies that provide such data, as partial reperfusion can affect final infarct volume.

Example 2: Closed-Form Solution

Objective

The goal of this example is to find a closed-form expression for the probability of a good outcome for an LVO patient depending on a given transport strategy. The rigorous theory underlying the following derivation can be found in Casella and Berger 2008. a detailed example application of this theory is included below.

Derivation

An objective of the disclosed example is to derive a closed-form expression for the marginal density function of $$U = V_p\left(1 - e^{-t/(V_p+\epsilon)}\right)I(V_p \geq 0, \epsilon \geq 0) \quad \text{Equation 8}$$

where U represents the infarct core volume and is a transformation of the random variables $V_p$~Beta representing penumbra volume and $\epsilon$~$f(\cdot)$ represents noise from a chosen distribution function. I is an indicator function included to clarify the domain of these variables. Note that $V_p \perp \epsilon$. As defined above, $\tau = V_p + \epsilon$, but in reality $\tau = f(V_p) + \epsilon$ where $f$ is a linear function. The former definition is included for simplicity, but the following derivations hold for the latter. The distribution of mRS outcomes can be easily recovered from the distribution of U, so those calculations are also omitted for simplicity. First a system of transformations is defined:

$$U = V_p\left(1 - e^{-t/(V_p+\epsilon)}\right) \quad \text{Equation 9}$$

$$W = V_p + \epsilon \quad \text{Equation 10}$$

The next step is to solve for $V_p(U,W)$ and $\epsilon(U,W)$. By Taylor Series expansion, it is possible to approximate $$1 - e^{-t/(V_p+\epsilon)} \approx \frac{t}{V_p+\epsilon} - \frac{1}{2}\left(\frac{t}{V_p+\epsilon}\right)^2 + \frac{1}{6}\left(\frac{t}{V_p+\epsilon}\right)^3 + O\left(\frac{1}{V_p^3}\right) \quad \text{Equation 11}$$

Note that this function can be approximated to arbitrary precision by including more terms in the series. For now, a first order approximation is used (which is surprisingly accurate per simulations in Desmos). Furthermore, note that as $t \rightarrow \infty$ the approximation gets worse, and as $\epsilon \rightarrow \infty$ the approximation gets better. It can be shown that $$U \approx V_p\left(\frac{t}{V_p+\epsilon}\right) \quad \text{Equation 12}$$

Because $W = V_p + \epsilon$, therefore $$U \approx V_p\left(\frac{t}{W}\right) \Rightarrow V_p = \frac{WU}{t} \quad \text{Equation 13}$$

Further, $$\epsilon = W - V_p = W - \frac{WU}{t} \quad \text{Equation 14}$$

It can be easily shown that the determinant of the Jacobian matrix is $$\left|\frac{d(V_p, \epsilon)}{d(U, W)}\right| = \frac{W}{t} \quad \text{Equation 15}$$

Finally, the desired marginal density of U is recovered by taking an integral:

$$f_U(u) = \int f_{V_p}(u, w) * f_\epsilon(u, w) * \frac{w}{t}dw \quad \text{Equation 16}$$

Full Taylor Series Expansion

U can be represented by the Taylor Series Expansion:

$$U = V_p\left(1 - e^{-\frac{t}{V_p+\epsilon}}\right) \approx V_p\left[\frac{t}{V_p+\epsilon} - \frac{1}{2}\left(\frac{t}{V_p+\epsilon}\right)^2 + \cdots + \frac{1}{d!}\left(\frac{t}{V_p+\epsilon}\right)^d\right] \quad \text{Equation 17}$$

$W=V_p+\epsilon$ and the goal is to get $V_p$ as a function of U, W. Therefore, substituting W into the above equation, $$U \approx V_p\left[\frac{t}{W} - \frac{1}{2}\left(\frac{t}{W}\right)^2 + \cdots + \frac{1}{d!}\left(\frac{t}{W}\right)^d\right] \quad \text{Equation 18}$$

Them isolating $V_p$ on one side of the equation yields $$V_p \approx \frac{U}{\frac{t}{w} - \frac{1}{2}\left(\frac{t}{W}\right)^2 + \cdots + \frac{1}{d!}\left(\frac{t}{W}\right)^d} \quad \text{Equation 19}$$

$$V_p \approx \frac{U * W^d}{tW^{d-1} - \frac{1}{2}tW^{d-2} + \cdots + \frac{1}{d!}t} \quad \text{Equation 20}$$

It is now possible to proceed with the Jacobian as outlined in previous derivations.

Example 3: Mobile Stroke Unit

Time is of essence when diagnosing and treating stroke. The conventional approach of bringing patients to the hospital is being re-evaluated with a more recent strategy of bringing the hospital to the patients via mobile stroke units. These units are capable of imaging the patient and giving them tPA on site before then bringing them to the hospital. It is still a challenge to determine the efficacy of these mobile stroke units, and insights and models are still needed to evaluate optimal placements of mobile stroke units to minimize delays in the region.

The below example evaluates the use of tools from graph theory to evaluate optimal mobile stroke unit home base placements. The road network of a region can be reconstructed as a graph with each intersection represented as a node and connecting roads represented as edges as seen in FIG. 17. This representation of the road network allows for leveraging some of the tools available in graph theory to calculate centrality of the network as a whole.

Potential stroke patients are not evenly distributed across any region in question. For example, stroke patients may be more densely populated in residential areas as opposed to commercial or industrial areas. There may be neighborhoods that are older, and thus at higher risk of strokes than other neighborhoods. These distributions can be taken into account in the graphs. This can either be done by using census data to determine the stroke risk for each node (or intersection), and thus weight the nodes that have higher risks as more important, or, for example, by using historical data of stroke calls to calculate the probability of where stroke patients are likely to come from.

Determining the appropriate metric that will be used to evaluate performance is critical. The ultimate goal of this example is to maximize good outcomes in stroke patients. In previous studies, it was shown that this can be accomplished using a physiological model of stroke growth over time, mapping the infarct volume to stroke outcomes. Using this model, the minimization of travel time from the mobile stroke unit home base to potential patients becomes a useful performance metric to optimize against.

Using this weighted graph and performance metric, graph theory was used to identify central nodes in this network. In graph theory, "closeness centrality" measures how close (the average shortest path length) a node is to all other nodes in the network. Mathematically, this is represented by:

$$C(X) = \frac{1}{\Sigma_y\ d(y, x)}, \quad \text{Equation 26}$$

where d(y,x) represents the distance between vertices x and y. To normalize this, the representation can be rewritten as $$C(X) = \frac{N-1}{\Sigma_y\ d(y, x)}, \quad \text{Equation 27}$$

where N represents the number of nodes in the graph, thus taking a weighted average of the distances.

The nodes with the smallest closeness centrality represent locations for a mobile stroke unit's home base which will be closest to all other points in the road network. Furthermore, this calculation of "shortest path length" can be computed based on travel times as opposed to distances, meaning that in some scenarios, the optimal mobile stroke unit home base may be at different points at different times of day, due to the traffic patterns during rush hour versus middle of the night, for example. These metrics can be calculated efficiently for large networks, and so provide real-time and/or periodic updates of where mobile stroke units should stay while waiting for the next call.

The closeness centrality metric works to identify one or more central mobile stroke unit home base(s). When including multiple mobile stroke units, the algorithm changes in order to include clustering analysis to subdivide the networks into smaller sub-units, each governed by a single mobile stroke unit. In some embodiments, some or all sub-units can change and shift as a mobile stroke unit may be called to a patient and thus be temporarily unavailable for any new calls. In the disclosed system, a real-time coordinating system is configured to account for mobile stroke units that are temporarily unavailable and adjusts the optimal location of remaining mobile stroke units given the change in coverage, if necessary.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

REFERENCES

The following publications are incorporated herein by reference in their entirety Saver J L. Time is brain—quantified. *Stroke.* 2006; 37(1): 263-266. doi:10.1161/01.STR.0000196957.55928.ab Bandera E, Botteri M, Minelli C, Sutton A, Abrams K, Latronico N. Cerebral Blood Flow Threshold of Ischemic Penumbra and Infarct Core in Acute Ischemic Stroke. *Stroke.* 2006; 37(5): 1334-1339. doi:10.1161/01.STR.0000217418.29609.22

Dozois A, Hampton L, Kingston C W, Lambert G, Porcelli T J, Sorenson D, Templin M, VonCannon S, Asimos A W. PLUMBER Study (Prevalence of Large Vessel Occlusion Strokes in Mecklenburg County Emergency Response). *Stroke.* 2017; 48(12):3397-3399. doi:10.1161/STROKEAHA.117.018925

Goyal M, Menon B, van Zwam W H, Dippel D W, Mitchell P, Demchuk A, Dávalos A, Majoie C, van der Lugt A, de Miquel M A, et al. Endovascular thrombectomy after large-vessel ischaemic stroke: a meta-analysis of individual patient data from five randomised trials. *Lancet Lond Engl.* 2016; 387(10029): 1723-1731. doi:10.1016/S0140-6736(16)00163-X Prabhakaran S, Ruff I, Bernstein R A. Acute stroke intervention: a systematic review. *JAMA.* 2015; 313(14): 1451-1462. doi:10.1001/jama.2015.3058

Powers W J, Rabinstein A A, Ackerson T, Adeoye M O, Bambakidis N C, Becker K, Biller J, Brown M, Demaerschalk B M, Hoh B, et al. Guidelines for the Early Management of Patients With Acute Ischemic Stroke: 2019 Update to the 2018 Guidelines for the Early Management of Acute Ischemic Stroke: A Guideline for Healthcare Professionals From the American Heart Association/American Stroke Association. *Stroke.* 2019; 50(12):e344-e418. doi:10.1161/STR.0000000000000211

Saver J L, Goyal M, van der Lugt A, Menon B K, Majoie C B, Dippel D W, Campbell B C, Nogueira R G, Demchuk A M, Tomasello A, et al. Time to Treatment With Endovascular Thrombectomy and Outcomes From Ischemic Stroke: A Meta-analysis. *JAMA.* 2016; 316(12): 1279-1289. doi:10.1001/jama.2016.13647

Fonarow G C, Zhao X, Smith E E, Saver J L, Reeves M J, Bhatt D L, Xian Y, Hernandez A F, Peterson E D, Scwhamm L H. Door-to-Needle Times for Tissue Plasminogen Activator Administration and Clinical Outcomes in Acute Ischemic Stroke Before and After a Quality Improvement Initiative. *JAMA.* 2014; 311(16):1632-1640. doi:10.1001/jama.2014.3203

Menon B K, Sajobi T T, Zhang Y, Rempel J L, Shuaib A, Thornton J, Williams D, Roy D, Poppe A Y, Jovin T G, et al. Analysis of Workflow and Time to Treatment on Thrombectomy Outcome in the Endovascular Treatment for Small Core and Proximal Occlusion Ischemic Stroke (ESCAPE) Randomized, Controlled Trial. *Circulation.* 2016; 133(23):2279-2286. doi:10.1161/CIRCULATIONAHA.115.019983

Southerland A M, Johnston K C, Molina C A, Selim M H, Kamal N, Goyal M. Suspected Large Vessel Occlusion. *Stroke.* 2016; 47(7): 1965-1967. doi:10.1161/STROKEAHA.115.011149

Texas Health and Human Services. Requirements for Stroke Facility Designation. Texas: Texas Department of State Health Services; 2008

Christoforidis G A, Vakil P, Ansari S A, Dehkordi F H, Carroll T J. Impact of Pial Collaterals on Infarct Growth Rate in Experimental Acute Ischemic Stroke. *Am J Neuroradiol.* 2017; 38(2):270. doi:10.3174/ajnr.A5003

Gomez C R. Time Is Brain: The Stroke Theory of Relativity. *J Stroke Cerebrovase Dis Off J Natl Stroke Assoc.* 2018; 27(8):2214-2227. doi:10.1016/j.jstrokecerebrovasdis.2018.04.001

Banks J L, Marotta C A. Outcomes Validity and Reliability of the Modified Rankin Scale: Implications for Stroke Clinical Trials. *Stroke.* 2007; 38(3):1091-1096. doi:10.1161/01.STR.0000258355.23810.c6

Ernst M, Boers A M, Aigner A, Berkhemer O, Yoo A J, Roos Y B, Dippel D W, van der Lugt A, van Oostenbrugge R, van Zwam W H, et al. Association of Computed Tomography Ischemic Lesion Location With Functional Outcome in Acute Large Vessel Occlusion Ischemic Stroke. *Stroke.* 2017; 48(9):2426-2433. doi:10.1161/STROKEAHA.117.017513

Vogt G, Laage R, Shuaib A, Schneider A. Initial lesion volume is an independent predictor of clinical stroke outcome at day 90: an analysis of the Virtual International Stroke Trials Archive (VISTA) database. *Stroke.* 2012; 43(5):1266-1272. doi:10.1161/STROKEAHA.111.646570

Malhotra K, Gornbein J, Saver J L. Ischemic Strokes Due to Large-Vessel Occlusions Contribute Disproportionately to Stroke-Related Dependence and Death: A Review. *Front Neurol.* 2017; 8:651. doi:10.3389/fneur.2017.00651

Markus R, Reutens D C, Kazui S, Read S, Wright P, Chambers B R, Sachinidis J I, Tochon-Danguy H J, Donnan G A. Topography and Temporal Evolution of Hypoxic Viable Tissue Identified by 18F-Fluoromisonidazole Positron Emission Tomography in Humans After Ischemic Stroke. *Stroke.* 2003; 34(11):2646-2652. doi:10.1161/01.STR.0000094422.74023.FF Rivers C S, Wardlaw J M, Armitage P A, Bastin M E, Carpenter T K, Cvoro V, Hand P J, Dennnis M S. Do Acute Diffusion- and Perfusion-Weighted MRI Lesions Identify Final Infarct Volume in Ischemic Stroke? *Stroke.* 2006; 37(1):98-104. doi:10.1161/01.STR.0000195197.66606.bb Gratz P P, Schroth G, Gralla J, Mattle H P, Fischer U, Jung S, Mordasini P, Hsieh K, Verma R K, Weisstanner C, El-Koussy M. Whole-Brain Susceptibility-Weighted Thrombus Imaging in Stroke: Fragmented Thrombi Predict Worse Outcome. *AJNR Am J Neuroradiol.* 2015; 36(7): 1277-1282. doi:10.3174/ajnr.A4275

Zanette E M, Roberti C, Mancini G, Pozzilli C, Bragoni M, Toni D. Spontaneous Middle Cerebral Artery Reperfusion in Ischemic Stroke. *Stroke.* 1995; 26(3):430-433. doi:10.1161/01.STR.26.3.430

Abilleira S, Ribera A, Cardona P, Rubiera M, López-Cancio E, Amaro S, Rodríguez-Campello A, Camps-Renom P, Cánovas D, Angels de Miquel M, et al. Outcomes After Direct Thrombectomy or Combined Intravenous and Endovascular Treatment Are Not Different. *Stroke.* 2017; 48(2):375-378. doi:10.1161/STROKEAHA.116.015857

Fischer U, Kaesmacher J, Pereira V M, Chapot R, Siddiqui A H, Froehler M T, Cognard C, Furlan A J, Saver J L, Gralla J. Direct Mechanical Thrombectomy Versus Combined Intravenous and Mechanical Thrombectomy in Large-Artery Anterior Circulation Stroke: A Topical Review. *Stroke.* 2017; 48(10):2912-2918. doi:10.1161/STROKEAHA.117.017208

Suzuki K, Matsumaru Y, Takeuchi M, Morimoto M, Kanazawa R, Takayama Y, Kamiya Y, Shigeta K, Okubo S, Hayakawa M, et al. Effect of Mechanical Thrombectomy Without vs With Intravenous Thrombolysis on Functional Outcome Among Patients With Acute Ischemic Stroke: The SKIP Randomized Clinical Trial. *JAMA.* 2021; 325(3):244-253. doi:10.1001/jama.2020.23522

Muchada M, Rodriguez-Luna D, Pagola J, Flores A, Sanjuan E, Meler P, Boned S, Alvarez-Sabin J, Ribo M, Molina C A, Rubiera M. Impact of Time to Treatment on Tissue-Type Plasminogen Activator-Induced Recanalization in Acute Ischemic Stroke. *Stroke.* 2014; 45(9):2734-2738. doi:10.1161/STROKEAHA.114.006222

Goyal M, Demchuk A M, Menon B K, Eesa M, Rempel J L, Thornton J, Roy D, Jovin T G, Willinsky R A, Sapkota B L, et al. Randomized Assessment of Rapid Endovascular Treatment of Ischemic Stroke. *N Engl J Med.* 2015; 372(11): 1019-1030. doi:10.1056/NEJMoa1414905

Seners P, Turc G, Naggara O, Henon H, Piotin M, Arquizan C, Cho T H, Narata A P, Lapergue B, Richard S, et al. Post-Thrombolysis Recanalization in Stroke Referrals for Thrombectomy. *Stroke.* 2018; 49(12): 2975-2982. doi: 10.1161/STROKEAHA.118.022335

Holodinsky J K, Williamson T S, Demchuk A M, Zhao H, Zhu L, Francis M J, Goyal M, Hill M D, Kamal N. Modeling Stroke Patient Transport for All Patients With Suspected Large-Vessel Occlusion. *JAMA Neurol.* 2018; 75(12): 1477-1486. doi:10.1001/jamaneurol.2018.2424

Mendelow A D, Gregson B A, Rowan E N, Murray G D, Gholkar A, Mitchell P M; STICH II Investigators. Early surgery versus initial conservative treatment in patients with Spontaneous Supratentorial Lobar Intracerebral Haematomas (STICH II): a randomised trial. Lancet. 2013; 382(9890):397-408. doi10.1016/S0140-6736(13)60986-1

Mayer S A, Brun N C, Begtrup K, Broderick J, Davis S, Diringer M N, Skolnick B E, Thorsten S; FAST Trial Investigators. Efficacy and safety of recombinant activated factor VII for acute intracerebral hemorrhage. N Engl J Med. 2008; 358(20):2127-2137. doi:10.1056/NEJMoa0707534

Anderson C S, Huang Y, Arima H, Heeley E, Skulina C, Parsons M W, Peng B, Li Q, Su S, Tao Q L, et al.; INTERACT Investigators. Effects of early intensive blood pressure-lowering treatment on the growth of hematoma and perihematomal edema in acute intracerebral hemorrhage: Intensive Blood Pressure Reduction in Acute Cerebral Haemorrhage Trial (INTERACT). Stroke. 2010; 41(2):307-312. doi:10.1161/STROKEAHA.109.561795

Wang X, Arima H, Heeley E, Delcourt C, Huang Y, Wang J, Stapf C, Robinson T, Woodward M, Chalmers J, Anderson C S; INTERACT2 Investigators. Magnitude of blood pressure reduction and clinical outcomes in acute intracerebral hemorrhage: intensive blood pressure reduction in acute cerebral hemorrhage trial study. Hypertension. 2015; 65(5):1026-1032. doi:10.1161/HYPERTENSIONAHA.114.05044

Steiner T, Poli S, Griebe M, Hüsing J, Hajda J, Freiberger A, Bendszus M, Bösel J, Christensen H, Dohmen C, et al. Fresh frozen plasma versus prothrombin complex concentrate in patients with intracranial haemorrhage related to vitamin K antagonists (INCH): a randomised trial. Lancet Neurol. 2016; 15(6):566-573. doi:10.1016/S1474-4422(16)00110-1

Hemphill J C 3rd, Greenberg S M, Anderson C S, Becker K, Bendok B R, Cushman M, Fung G L, Goldstein J N, Macdonald R L, Mitchell P H, Scott P A, Selim M H, Woo D; on behalf of the American Heart Association Stroke Council, Council on Cardiovascular and Stroke Nursing, and Council on Clinical Cardiology. Guidelines for the management of spontaneous intracerebral hemorrhage: a guideline for healthcare professionals from the American Heart Association/American Stroke Association. Stroke. 2015; 46:2032-2060.

Menon B K, Al-Ajlan F S, Najm M, Puig J, Castellanos M, Dowlatshahi D, Calleja A, Sohn S, Ahn S H, Poppe A, et al. Association of Clinical, Imaging, and Thrombus Characteristics With Recanalization of Visible Intracranial Occlusion in Patients With Acute Ischemic Stroke. *JAMA.* 2018; 320(10):1017-1026. doi:10.1001/jama.2018.12498

Higashida R, Alberts M J, Alexander D N, Crocco T J, Demaerschalk B M, Derdeyn C P, Goldstein L B, Jauch E C, Mayer S A, Meltzer N M, et al. Interactions Within Stroke Systems of Care. *Stroke.* 2013; 44(10):2961-2984. doi:10.1161/STR.0b013e3182a6d2b2

United States Census Bureau. Tiger/Line Shapefiles with Selected Demographic and Economic Data. Last revised December 2019. Retrieved from: https://www.census.gov/geographies/mapping-files/2010/geo/tiger-data.

Zhao H, Coote S, Pesavento L, Churilov L, Dewey H M, Davis S M, Campbell B C V. Large Vessel Occlusion Scales Increase Delivery to Endovascular Centers Without Excessive Harm From Misclassifications. *Stroke.* 2017; 48(3):568-573. doi:10.1161/STROKEAHA.116.016056

Venema E, Lingsma H F, Chalos V, Mulder M J, Lahr M M, van der Lugt A, van Es A C, Steyerberg E W, Hunink M M, Dippel D W, et al. Personalized Prehospital Triage in Acute Ischemic Stroke. *Stroke.* 2019; 50(2):313-320. doi: 10.1161/STROKEAHA.118.022562

Xu Y, Parikh N S, Jiao B, Willey J Z, Boehme A K, Elkind M S. Decision Analysis Model for Prehospital Triage of Patients With Acute Stroke. *Stroke.* 2019; 50(4):970-977. doi:10.1161/STROKEAHA.118.023272

Holodinsky J K, Williamson T S, Kamal N, Mayank D, Hill M D, Goyal M. Drip and Ship Versus Direct to Comprehensive Stroke Center. *Stroke.* 2017; 48(1):233-238. doi: 10.1161/STROKEAHA.116.014306

Milne M S, Holodinsky J K, Hill M D, Nygren A, Qui C, Goyal M, Kamal N. Drip 'n Ship Versus Mothership for Endovascular Treatment. *Stroke.* 2017; 48(3):791-794. doi:10.1161/STROKEAHA.116.015321

Marc Ribo. European Stroke Organisation-World Stroke Organisation (ESO-WSO) Conference 2020: Presented Nov. 7, 2020. First Press Release. https://eso-wso-conference.org/media-portal/

Jahan R, Saver J L, Schwamm L H, Fonarow G C, Lian L, Matsouaka R A, Xian Y, Holms D N, Peterson E D, Yavagal D, et al. Association Between Time to Treatment With Endovascular Reperfusion Therapy and Outcomes in Patients With Acute Ischemic Stroke Treated in Clinical Practice. *JAMA.* 2019; 322(3):252-263. doi:10.1001/jama.2019.8286

What is claimed is:

1. A method of calculating a set of desired transport routes for a stroke patient, comprising:

selecting a set of destination points, the set of destination points comprising at least a first stroke center and a second stroke center;

from a patient starting point, generating a set of simulated infarct core growth models for simulated stroke patients along at least a first path from the patient starting point to the first stroke center followed by an optional trip to the second stroke center, and a second path from the starting point directly to the second stroke center;

varying a set of parameters of the simulated stroke patients across the set of simulated infarct core growth models;

calculating a probabilistic model of patient outcomes from the set of simulated infarct core growth models from the patient starting point; and designating whether the first path or the second path is preferable based on the probabilistic model.

2. The method of claim 1, further comprising selecting a set of origin points;

from each origin point of the set of origin points, generating a set of simulated infarct core growth models for simulated stroke patients along at least the first path and the second path;

calculating the probabilistic model of patient outcomes from the set of simulated infarct core growth models from each origin point; and designating, for each origin point, whether the first path or the second path is preferable based on the probabilistic model.

3. The method of claim 2, wherein the set of origin points are arranged in a grid.

4. The method of claim 1, wherein the first stroke center and the second stroke center are each of a type selected from a primary stroke center, a comprehensive stroke center, a primary plus stroke center, a thrombectomy capable stroke center, or an acute stroke ready hospital.

5. The method of claim 4, wherein the type of the first stroke center is different from the type of the second stroke center.

6. The method of claim 5, wherein the first stroke center is a primary stroke center and the second stroke center is a comprehensive stroke center.

7. The method of claim 1, wherein at least one simulated infarct core growth model along the first path includes simulation of cerebrovascular imaging of the patient and simulation of administering intravenous tissue plasminogen activator to the patient.

8. The method of claim 7, wherein the at least one simulated infarct core growth model along the first path further includes determining whether the simulated patient has a large vessel occlusion, and proceeding to the second stroke center if the large vessel occlusion is identified.

9. The method of claim 1, wherein the parameters are selected from the initial infarct core volume, the total volume of at-risk tissue encompassed by the ischemic penumbra, or the collateral-dependent time constant.

10. The method of claim 1, wherein the simulated infarct core growth models are generated via Monte Carlo simulations or a closed-form solution.

11. The method of claim 1, wherein the set of parameters comprises at least one patient-specific parameter selected from patient age, race, gender, height, weight, suspected time since stroke onset, or comorbidities.

12. The method of claim 1, wherein the set of parameters comprises at least one environmental parameter selected from time of day, traffic conditions, demographic/census data in the vicinity of the patient starting point, or hospital waiting time.

13. The method of claim 1, further comprising modifying at least one range of at least one parameter of the set of parameters based on additional information collected specific to a patient.

14. The method of claim 13, further comprising recalculating the probabilistic model of patient outcomes from the patient starting point using the modified parameters.

15. The method of claim 1, further comprising modifying at least one range of at least one parameter of the set of parameters based on additional information specific to a stroke network.

16. The method of claim 1, further comprising modifying at least one range of at least one parameter of the set of parameters based on additional information specific to an area in a vicinity of the patient starting point.

17. The method of claim 1, further comprising transmitting the destination of the designated path and an estimated time of arrival to a database.

18. A system for displaying a desired transport route for a stroke patient, comprising a computing device communicatively connected to a GPS receiver, and having a non-transitory computer-readable medium with instructions stored thereon, which when executed by a processor perform steps comprising:

receiving, from the GPS receiver, a starting point;

generating a set of simulated infarct core growth models for simulated stroke patients along at least a first path to a first stroke center followed by an optional trip to second stroke center, and a second path directly to the second stroke center, including querying travel time under current traffic and weather conditions along the first and second paths;

varying a set of parameters of the simulated stroke patients across the set of simulated infarct core growth models;

calculating a probabilistic model of patient outcomes from the set of simulated infarct core growth models from the patient starting point; and designating whether the first path or the second path is preferable based on the probabilistic model.

19. The system of claim 18, the steps further comprising:

selecting a closest origin point to the origin position from a database of origin points;

querying a desired transport route for a stroke patient from the database, corresponding to the closest origin point;

displaying, on a display, a desired transport route for a stroke patient from the closest origin point; and periodically updating the database of origin points by performing steps comprising:

from each origin point of the database of origin points, generating a set of simulated infarct core growth models for simulated stroke patients along at least a first path to a primary stroke center followed by an optional trip to a comprehensive stroke center, and a second path directly to the comprehensive stroke center, including querying travel time under current traffic and weather conditions along the first and second paths;

varying a set of parameters of the simulated stroke patients across the set of simulated infarct core growth models;

calculating a probabilistic model of patient outcomes from the set of simulated infarct core growth models from each origin point; and designating, for each origin point, whether the first path or the second path is preferable based on the probabilistic model.

20. The system of claim 19, further comprising at least one remote computing device communicatively connected to the computing device, and comprising a non-transitory computer-readable medium comprising the database.

21. The system of claim 18, the steps further comprising modifying at least one range of at least one parameter of the set of parameters based on additional information collected specific to the stroke patient.

22. The system of claim 21, the steps further comprising recalculating the probabilistic model of patient outcomes from the patient starting point using the modified parameters.

23. The system of claim 18, further comprising at least one sensor communicatively connected to the computing device and configured to record data related to the patient, the computing device further configured to receive the data from the sensor.

24. The system of claim 23, wherein the sensor is selected from a sound sensor, a temperature sensor, a pressure sensor, or an ambient light sensor.

25. The system of claim 23, the steps further comprising displaying the data received from the sensor on the display.

26. The system of claim 18, wherein the computing device is a smartphone, a laptop, or a tablet.

27. The system of claim 18, further comprising a vehicle, the vehicle comprising the computing device.

28. A method of calculating a preferred location for a mobile treatment unit in a geographic region, comprising:

obtaining a weighted graph representation of a road network in a geographic region, comprising a set of weighted nodes corresponding to intersections in the road network and a set of weighted edges corresponding to connecting roads between the nodes;

adjusting a weight of at least one node based on a calculated stroke risk at or near the corresponding intersection;

calculating a closeness centrality of one or more nodes in the weighted graph; and selecting at least one node of the one or more nodes in the weighted graph having the smallest closeness centrality as a preferred location for a mobile treatment unit.

29. The method of claim 28, wherein the mobile treatment unit is a mobile stroke treatment unit.

30. The method of claim 28, further comprising the steps of:

obtaining traffic information for one or more roads in the geographic region;

adjusting at least one weight of the set of weighted edges to account for expected additional travel time on the corresponding road due to increased traffic; and recalculating the closeness centrality of one or more nodes in the weighted graph.

31. The method of claim 28, wherein the at least one node comprises a plurality of nodes, corresponding to a plurality of mobile treatment units; and further comprising the steps of:

receiving a communication that one of the plurality of mobile treatment units is unavailable;

recalculating the closeness centrality of the plurality of nodes in the weighted graph; and selecting at least one different node of the plurality of nodes in the weighted graph to redeploy the remaining mobile treatment units of the plurality of mobile treatment units.

* * * * *